United States Patent
Chakrabarty et al.

(10) Patent No.: US 7,338,766 B2
(45) Date of Patent: Mar. 4, 2008

(54) COMPOSITIONS AND METHODS FOR TREATING MALARIA WITH CUPREDOXIN AND CYTOCHROME

(75) Inventors: Ananda Chakrabarty, Villa Park, IL (US); Tapas Das Gupta, River Forest, IL (US); Tohru Yamada, Oak Park, IL (US); Anita Chaudhari, Clifton Park, NY (US); Arsenio Fialho, Lisbon (PT); Chang Soo Hong, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/436,590

(22) Filed: May 19, 2006

(65) Prior Publication Data

US 2006/0251669 A1    Nov. 9, 2006

Related U.S. Application Data

(63) Continuation-in-part of application No. 10/720,603, filed on Nov. 24, 2003, which is a continuation-in-part of application No. 10/047,710, filed on Jan. 15, 2002, now Pat. No. 7,084,105.

(60) Provisional application No. 60/682,813, filed on May 20, 2005, provisional application No. 60/680,500, filed on May 13, 2005, provisional application No. 60/616,782, filed on Oct. 7, 2004, provisional application No. 60/414,550, filed on Aug. 15, 2003, provisional application No. 60/780,868, filed on Mar. 10, 2003, provisional application No. 60/269,133, filed on Feb. 15, 2001.

(51) Int. Cl.
*C12Q 1/68* (2006.01)
*C12P 21/04* (2006.01)
*A61K 38/00* (2006.01)
*A61K 38/44* (2006.01)
*C07K 14/445* (2006.01)

(52) U.S. Cl. .................. 435/6; 435/69.7; 435/258.1; 435/258.2; 424/185.1; 424/94.4; 514/2; 514/12; 530/300; 530/350

(58) Field of Classification Search ............. 435/191.1, 435/268.1, 6, 69.7, 258.2; 424/185.1, 94.4; 514/2, 12; 530/300, 350
See application file for complete search history.

(56) References Cited

U.S. PATENT DOCUMENTS 6,551,795 B1 *  4/2003  Rubenfield et al. ........ 435/69.1
2003/0059436 A1  3/2003  Chishti rt al. ............ 424/185.1

FOREIGN PATENT DOCUMENTS

WO    WO 02/76380 A3    10/2002
WO    WO 2005018662 A1    3/2005

OTHER PUBLICATIONS

Fundamental Immunology 242 (William E. Paul, M.D. ed ., 3d ed. 1993).*
Accession No. P00282.*
Hoitink et al Gene vol. 90, Issue 1, May 31, 1990, pp. 15-20.*
Canters and Gilardi FEBS Letters vol. 325, Issues 1-2, Jun. 28, 1993, pp. 39-4.*
Nar et al FEBS Letters vol. 306, Issues 2-3, Jul. 20, 1992, pp. 119-124.*
Kamp et al Biochimica et Biophysica Acta (BBA)—Bioenergetics vol. 1019, Issue 3, Sep. 19, 1990, pp. 283-292.*
Yamada T, et al., "Internalization of bacterial redox protein azurin in mammalian cells: entry domain and specificity", *Cell Microbiol.* Oct. 2005;7(10);1418-31.
Yamada T, et al., "Rusticyanin, a bacterial electron transfer protein, causes G1 arrest in J774 and apoptosis in human cancer cells", *Cell Cycle* Sep. 2004;3(9):1182-7.
Yamada T, et al., "Regulation of mammalian cell growth and death by bacterial redox proteins: relevance to ecology and cancer therapy", *Cell Cycle* Jun. 2004;3(6):752-5.
Hiraoka Y, et al., "Modulation of mammalian cell growth and death by prokaryotic and eukaryotic cytochrome c", *Proc Natl Acad Sci U S A*. Apr. 27, 2004;101(17):6427-32.
Yamada T, et al., "Apoptosis or growth arrest: Modulation of tumor suppressor p53's specificity by bacterial redox protein azurin", *Proc Natl Acad Sci U S A*. Apr. 6, 2004;101(14):4770-5.
Punj V, et al., "Bacterial cupredoxin azurin as an inducer of apoptosis and regression in human breast cancer", *Oncogene* Mar. 25, 2004;23(13):2367-78.
Chakrabarty Am, "Microorganisms and Cancer: Quest for a Therapy", *J. Bacteriol.* 185(9):2683-86.
Punj V, et al., "Bacterial *Cupredoxin azurin* and its interactions with the tumor suppressor protein p53", *Biochem Biophys Res Commun.* Dec. 5, 2003;312(1):109-14.

(Continued)

*Primary Examiner*—Susan Ungar
*Assistant Examiner*—Padma Baskar
(74) *Attorney, Agent, or Firm*—Sheppard Mullin Richter & Hampton LLC

(57) ABSTRACT

The present invention relates to cupredoxin and cytochrome and their use, separately or together, to inhibit the spread of parasitemia in mammalian red blood cells and other tissues infected by the malaria parasite, and in particular the parasitemia of human red blood cells by *P. falciparum*. The invention provides isolated peptides that are variants, derivatives or structural equivalents of cupredoxins or cytochrome c, and compositions comprising cupredoxins and/or cytochrome c, or variants, derivatives or structural equivalents thereof, that are useful for treating or preventing malaria infection in mammals. Further, the invention provides methods to treat mammalian patients to prevent or inhibit the growth of malarial infection in mammals. The invention also provides methods to prevent the growth of malaria infection in insect vectors.

8 Claims, 3 Drawing Sheets

OTHER PUBLICATIONS

Figure 1:
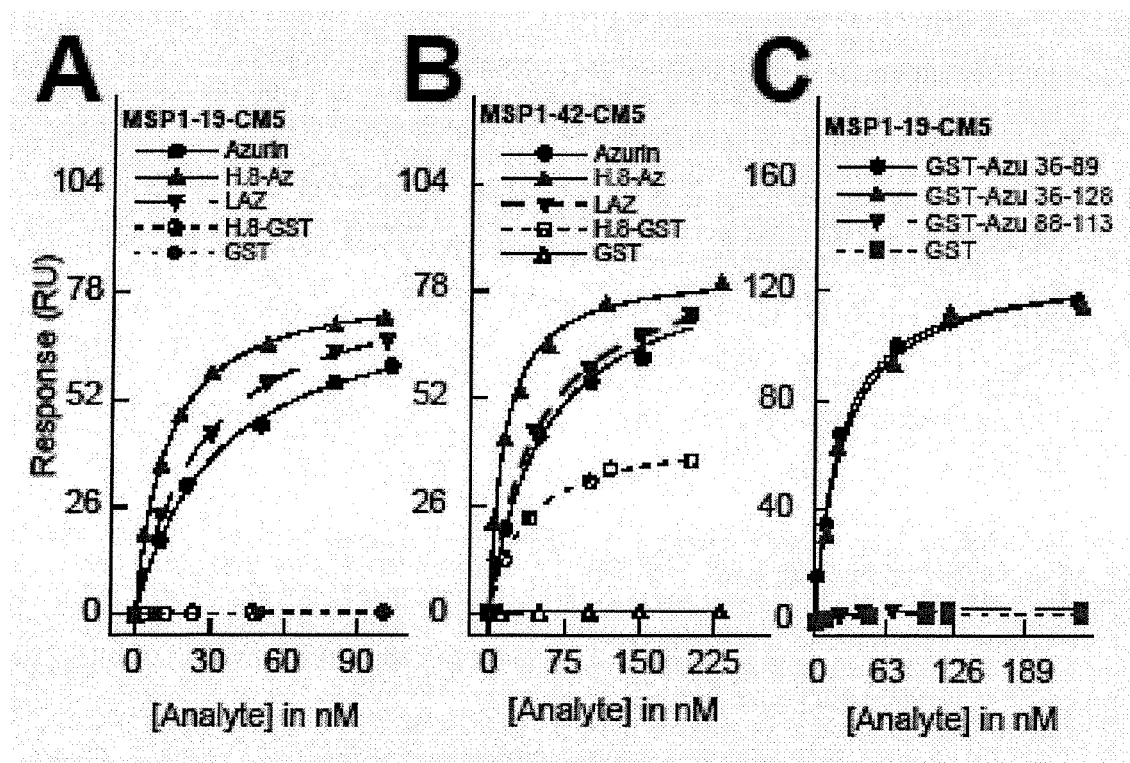

Punj V, et al., "Energy-generating enzymes of *Burkholderia cepacia* and their interactions with macrophages", *J Bacteriol.* May 2003;185(10):3167-78.

Goto M, et al., "Induction of apoptosis in macrophages by *Pseudomonas aeruginosa* azurin: tumour-suppressor protein p53 and reactive oxygen species, but not redox activity, as critical elements in cytotoxicity", *Mol Microbiol.* Jan. 2003; 47(2):549-59.

Yamada T, et al., "The Bacterial redox protein azurin induces apoptosis in J774 macrophages through complex formation and stabilization of the tumor suppressor protein p53", *Infect Immun.* Dec. 2002;70(12):7054-62.

Yamada T, et al., "Bacterial redox protein azurin, tumor suppressor protein p53, and regression of cancer", *Proc Natl Acad Sci U S A.* Oct. 29, 2002;99(22):14098-103. Epub Oct. 22, 2002.

Zaborina O, et al., "P2Z-Independent and P2Z receptor-mediated macrophage killing by *Pseudomonas aeruginosa* isolated from cystic fibrosis patients", *Infect Immun.* Oct. 1999; 67(10):5231-42.

Zaborina O, et al., "Secreted products of a nonmucoid *Pseudomonas aeruginosa* strain induce two modes of macrophage killing: external-ATP-dependent, P2Z-receptor-mediated necrosis and ATP-independent, caspase-mediated apoptosis", *Microbiology* , Oct. 2000;146 (Pt 10):2521-30.

Yang D., et al., "Bacterial redox protein azurin induce apoptosis in human osteosarcoma U2OS cells", *Pharmacological Research* 2005 52(5):413-421.

Apiyo D. and Wittung-Stafshede, P., "Unique complex between bacterial azurin and tumor-suppressor protein p53", *Bioche. Biophys. Res. Comm.* 2005 332: 965-968.

Ye, Z., et al. "Selective inducement effect of bacterial redox protein azurin on apoptosis of human osteosarcoma cell line U2OS", *Chinese Journal of Cancer* 2005, 24(3): 298-304.

Yamada et al., "The Bacterial Redox Protein Azurin Induces Apoptosis in J774 Macrophages through Complex Formation and Stabilization of the Tumor Suppressor Protein p53", *Infection and Immunity*, vol. 70(12), Dec. 2002, pp. 7054-7062.

Anonymous: "Plastocyanin precursor" Database EMBL, Online, Nov. 1, 1997, XP002306632 abstract.

Anonymous: "Rusticyanin precursor" Database EMBL, Online, Mar 1, 1992, XP002306633 abstract.

Anonymous: "Pseudoazurin precursor" Database EMBL, Online, Feb. 1, 1991, XP002306634 abstract.

Navy Environment Health Center; Bureau of Medicine and Surgery. "Navy Medical Dept. Pocket Guide to Malaria Prevention and Control." Technical Manual NEHC-TM PM 6250.1 (Sep. 2000).

\* cited by examiner

COMPOSITIONS AND METHODS FOR TREATING MALARIA WITH CUPREDOXIN AND CYTOCHROME

RELATED APPLICATIONS

This application claims priority to co-filed U.S. Provisional Patent Application Ser. No. 11/436,591, entitled "Compositions and Methods for Treating HIV Infection with Cupredoxin and Cytochrome c", filed May 19, 2006, U.S. Provisional Patent Application Ser. No. 60/780,868, filed Mar. 10, 2006, U.S. Provisional Patent Application Ser. No. 60/682,813, filed May 20, 2005, and U.S. patent application Ser. No. 11/244,105, filed Oct. 6, 2005, which claims priority to U.S. Provisional Patent Application Ser. No. 60/616,782, filed Oct. 7, 2004, and U.S. Provisional Patent Application Ser. No. 60/680,500, filed May 13, 2005, and is a continuation-in-part of U.S. patent application Ser. No. 10/720,603, filed Nov. 24, 2003, which claims priority to U.S. Provisional Patent Application Ser. No. 60/414,550, filed Aug. 15, 2003, and which is a continuation-in-part of U.S. patent application Ser. No. 10/047,710, filed Jan. 15, 2002, now U.S. Pat. No. 7,084,105 which claims priority to U.S. Provisional Patent Application Ser. No. 60/269,133, filed Feb. 15, 2001. The entire content of these prior applications is fully incorporated herein by reference.

STATEMENT OF GOVERNMENTAL INTEREST

The subject matter of this application has been supported by research grants from the National Institutes of Health (NIH), Bethesda, Md., U.S.A., (Grant Numbers AI 16790-21, ES 04050-16, AI 45541, CA09432 and N01-CM97567). The government may have certain rights in this invention.

FIELD OF THE INVENTION

The present invention relates to cupredoxin and cytochrome and their use, separately or in combination, in inhibiting parasitemia of the malaria parasite, and in particular inhibiting parasitemia of *Plasmodium falciparum* in mammalian red blood cells. The invention also relates to variants and derivatives of cupredoxin and cytochrome that retain the ability to inhibit parasitemia by the malaria parasite. Finally, the invention provides methods to inhibit the spread of malaria infection in insect vectors.

BACKGROUND

About one quarter of the world's population is exposed to the risk of malaria and more than a million people die of malaria each year. Of the four species of malarial parasites that infect humans, the two major species are *Plasmodium falciparum* and *P. vivax*.

The *P. falciparum* blood stage merozoites bind to and parasitize the erythrocytes using a variety of surface proteins (Cowman et al., FEBS Lett. 476:84-88 (2000); Baum et al., J. Biol. Chem. 281:5197-5208 (2006)), a major antigenic member of which is called Merozoite Surface Protein 1 (MSP1), a 195 kDa protein. MSP1 is present in all the erythrocyte-invasive species of *Plasmodium*, anchored to the merozoite surface by a glycosyl-phosphatidylinositol linkage. During early stages of the erythrocyte invasion process, soon after release from infected erythrocytes, the merozoite MSP1 protein undergoes proteolytic cleavage, producing a C-terminal cleavage product MSP1-42, which subsequently undergoes a second cleavage, producing an 11 kDa peptide MSP1-19, which remains attached to the parasite surface as it enters the erythrocyte. The formation of the cleavage product MSP1-19 is very important for successful invasion by the parasite since inhibition of its proteolytic formation or its neutralization by monoclonal antibodies prevents entry of the parasite to the erythrocytes (Blackman et al., J. Exptl., Med. 180:389-393 (1994)).

The MSP1-19 peptide is one of the most important malaria vaccine candidates available. MSP1-19-specific antibodies from malaria-resistant human sera react with the antigen and include a major erythrocyte-invasion inhibitory component (Holder & Riley, Parasitol. Today, 12: 173-174 (1996); O'Donnell et al., *J. Expt. Med.* 193: 1403-1412 (2001)). Serum from donors in malaria-endemic regions usually demonstrates strong antibody reactivity towards Pf MSP1-19. (Nwuba et al., Infect. Immun. 70: 5328-5331 (2002))

The monoclonal antibody (mAb) G17.12 was raised against recombinant Pf MSP1-19 and recognizes its epitope on the parasite surface, demonstrating that this region of the antigen is accessible on the native MSP1 polypeptide complex (Pizarro et al., J. Mol. Biol. 328:1091-1103 (2003)). Interestingly, erythrocyte invasion experiments in vitro showed that infection is not inhibited in the presence of G17.12, even at 200 μg/ml concentration and G17.12 does not inhibit in vitro secondary processing of MSP1. Id. The presence of antibodies that block the binding of invasion—inhibitory antibodies, thereby facilitating parasite survival, has also been demonstrated (Guevara Patino et al., J. Expt. Med. 186: 1689-1699 (1997)), and may be responsible for the failure of G17.12 mAb to inhibit erythrocyte invasion by *M. falciparum*.

Cerebral malaria, a rare but fatal infection restricted to *P. falciparum* invasion of brain capillaries because of the sequestration of parasitized erythrocytes, is often untreatable because most drugs cannot cross the blood-brain barrier to reach the brain capillaries. Adhesion of *P. falciparum*—infected erythrocytes to brain capillaries is mediated by the interaction of parasite ligands Pf Emp-1 family of proteins expressed on the surface of infected erythrocytes with ICAM-1 and CD36 expressed on the surface of capillary endothelium cells in cerebral vessels. (Smith et al., Proc. Natl. Acad. Sci. USA 97:1766-1771 (2000); Franke-Fayard et al., Proc. Natl. Acad. Sci. USA 102, 11468-11473 (2005))

Although a few drugs, such as chloroquine that targets the heme detoxification pathway, are used to treat malaria, there are increasing incidence of parasite resistance to drugs and mosquito vector resistance to insecticides. Chloroquine antagonizes heme polymerization mediated by parasite-induced HRPs (histidine-rich proteins), as heme monomers are highly toxic for malaria parasites. The polymerization of heme allows detoxification, which is reversed by chloroquine. Another drug, artemisinin, is effective against chloroquine-resistant *P. falciparum* in cerebral malaria. Artemisinin forms adducts with globin-bound heme in hemoglobin, which binds HRPs to prevent heme polymerization. There is an urgent need to find new drugs for this dreaded disease that is particularly prevalent in Africa and Asia. Present attempts at drug development are directed towards deciphering the complete parasite genome sequence, molecular modeling of the malaria parasite proteins and a search for novel drug targets.

SUMMARY OF THE INVENTION

The present invention relates to cupredoxin and cytochrome and their use, separately or together, to inhibit the spread of parasitemia in mammalian red blood cells and other tissues infected by the malaria parasite, and in particular the parasitemia of human red blood cells by *P. falciparum*.

One aspect of the invention is an isolated peptide that is a variant, derivative or structural equivalent of a cupredoxin or cytochrome; and that can inhibit intracellular replication of a malarial parasite in malaria-infected human red blood cells.

Another aspect of the invention is an isolated peptide that is a variant, derivative or structural equivalent of a cupredoxin; and that can bind a protein selected from the group consisting of PfMSP1-19 and PfMSP1-42.

Another aspect of the invention is an isolated peptide that is a variant, derivative or structural equivalent of a cupredoxin or cytochrome, and that can inhibit parasitemia by malaria in malaria-infected red blood cells. Specifically, the isolated peptide can inhibit parasitemia by malaria in *P. falciparum*-infected human red blood cells. In some embodiments, the cupredoxin is an azurin, pseudoazurin, plastocyanin, rusticyanin, Laz or auracyanin. Specifically, the cupredoxin may be rusticyanin, azurin or Laz. In some embodiments, the cupredoxin is from *Pseudomonas aeruginosa, Alcaligenes faecalis, Achromobacter xylosoxidan, Bordetella bronchiseptica, Methylomonas* sp., *Neisseria meningitidis, Neisseria gonorrhea, Pseudomonas fluorescens, Pseudomonas chlororaphis, Xylella fastidiosa* or *Vibrio parahaemolyticus*. Specifically, the cupredoxin may be from *Thiobacillus ferrooxidans, Pseudomonas aeruginosa, Neisseria gonorrhea* or *Neisseria meningitidis*.

In other embodiments of this aspect, the cytochrome is cytochrome c or cytochrome f. In particular, the cytochrome c may be from human or *Pseudomonas aeruginosa*. The cytochrome f may be from a cyanobacteria.

In other embodiments of this aspect, the isolated peptide is a truncation of a peptide selected from the group consisting of SEQ ID NOS: 1-20 and 22. In some embodiments, SEQ ID NOS: 1-20 or 22 has at least 90% amino acid sequence identity to the sequence of the isolated peptide.

In some embodiments of this aspect, the isolated peptide is a truncation of cupredoxin or cytochrome. In some embodiments, the isolated peptide is more than about 10 residues and not more than about 100 residues. The isolated peptide may comprise azurin residues 36-89. Alternatively, the isolated peptide may consist of azurin residues 36-89. Alternatively, the isolated peptide may comprise equivalent residues of a cupredoxin as azurin 36-89.

In other embodiments of this aspect, the isolated peptide is fused to a H.8 region of Laz. In another embodiment, the isolated peptide is a structural equivalent of monoclonal antibody G17.12.

Another aspect of the invention is a composition comprising at least one cupredoxin, cytochrome, or isolated peptide that is a variant, derivative or structural equivalent of a cupredoxin or cytochrome that can inhibit parasitemia by malaria in malaria-infected red blood cells, in a pharmaceutical composition. Specifically, the pharmaceutical composition may be formulated for intravenous administration. The composition may comprise another anti-malarial drug or an anti-HIV drug.

In some embodiments of the composition, the cupredoxin is from *Pseudomonas aeruginosa, Alcaligenes faecalis, Achromobacter xylosoxidan, Bordetella bronchiseptica, Methylomonas* sp., *Neisseria meningitidis, Neisseria gonorrhea, Pseudomonas fluorescens, Pseudomonas chlororaphis, Xylella fastidiosa* or *Vibrio parahaemolyticus*. Specifically, the cupredoxin may be from *Thiobacillus ferrooxidans, Pseudomonas aeruginosa, Neisseria gonorrhea* or *Neisseria meningitidis*.

In some embodiments of the composition, the cytochrome is cytochrome c or cytochrome f. Specifically, the cytochrome c may be from human or *Pseudomonas aeruginosa*. The cytochrome f may be from a cyanobacteria. In some embodiments, the cupredoxin or cytochrome c is SEQ ID NOS: 1-20 or 22.

Another aspect of the invention is a method to treat a patient suffering from an infection by a malaria parasite by administering to the patient an effective amount of the composition of the invention. In specific embodiments, the peptide inhibits parasitemia by malaria in the patient's malaria-infected human red blood cells. In some embodiments, the malaria parasite is *Plasmodium vivax* or *Plasmodium falciparum*. In some embodiments, the patient is additionally suffering from HIV infection. In some embodiments, the composition is administered with a second composition that may contain an anti-malarial drug and/or an anti-HIV drug. In some embodiments, the composition of the invention is administered within 0 minutes to 12 hours of the administration of second composition. In some embodiments, the composition of the invention is administered to the patient orally, by inhalation, intravenously, intramuscularly or subcutaneously; and, specifically, the composition may be administered to the patient intravenously.

Another aspect of the invention is a method to treat a patient suspected of having contact with a malaria parasite, comprising administering to the patient an effective amount of the composition of the invention.

Another aspect of the invention is a method to prevent malaria in mammals, comprising administering to an insect vector in a population of insect vectors harboring a malaria parasite an amount of the composition of the invention. In some embodiments of this method, the composition is administered to the insect vector orally.

These and other aspects, advantages, and features of the invention will become apparent from the following figures and detailed description of the specific embodiments.

BRIEF DESCRIPTION OF THE FIGURES

FIG. 1. FIG. 1 depicts surface plasmon resonance binding titrations depicting the interactions of Azurin, H.8-azurin (H.8-Az), Laz, and GST-azurin (GST-Azu) constructs with MSP1-19 and MSP1-42. (A) Binding curves demonstrating the interactions of azurin and its analogues with MSP1-19 immobilized on carboxymethyldextran coated gold sensor chips (MSP1-19-CM5). Concentration dependent binding of the azurin proteins to MSP1-19 was determined via injection of various concentrations (0.05-300 nM) over the sensor surface and the extent of binding was evaluated as a function of the equilibrium resonance response value measured in resonance units (RU). While H.8-Az and Laz bound somewhat more strongly than azurin, no binding was seen with GST or H.8-GST. (B) In vitro binding titrations for immobilized MSP1-42 with azurin and its analogues was followed in a similar manner to that for MSP1-19 as shown in (A). Relative binding affinities were determined via fitting the data to Req=Rmax/(1+(Kd/C)) with the curve fits connecting the data points in the graphs. The MSP1-19 binding Kd values are: 32.2±2.4 nM (azurin), 26.2±2.4 nM (Laz), 11.8±0.3 nM (H.8-Az), and those for MSP1-42 binding are: 54.3±7.6 nM (azurin), 45.6±2.4 nM (Laz) and 14.3±1.7 nM (H.8-Az). (C) Binding titrations for the interactions of GST-Azu fusion proteins over the MSP1-19-CM5 sensors surface demonstrate the recognition of GST-Azu 36-128 and GST-Azu 36-89 with MSP1-19. No binding was seen with GST or GST-Azu 88-113.

Figure 2:
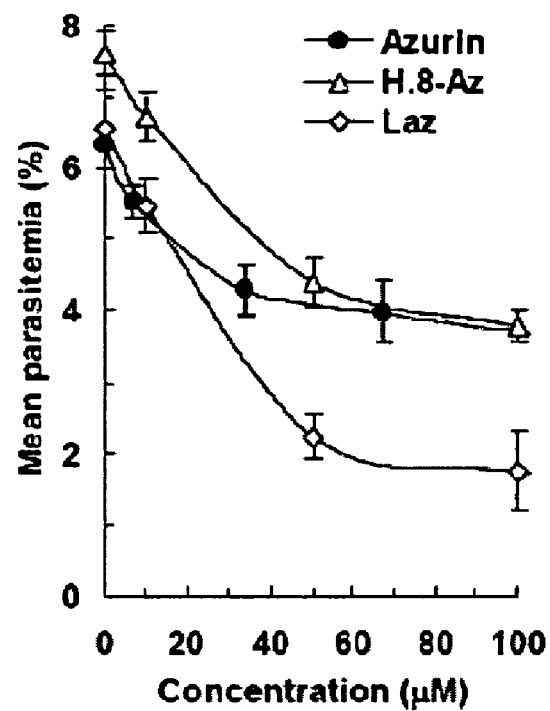

FIG. 2. FIG. 2 depicts inhibition of *P. falciparum* parasitemia (parasite growth within the RBC) by different concentrations, as shown, of Azurin, H.8-azurin (H.8-Az) and Laz. In these experiments, normal red blood cells were infected with schizonts in absence or in presence of the proteins at different concentrations, incubated overnight and the number of intracellular parasites was scored by thin blood smear and Giemsa staining.

Figure 3:
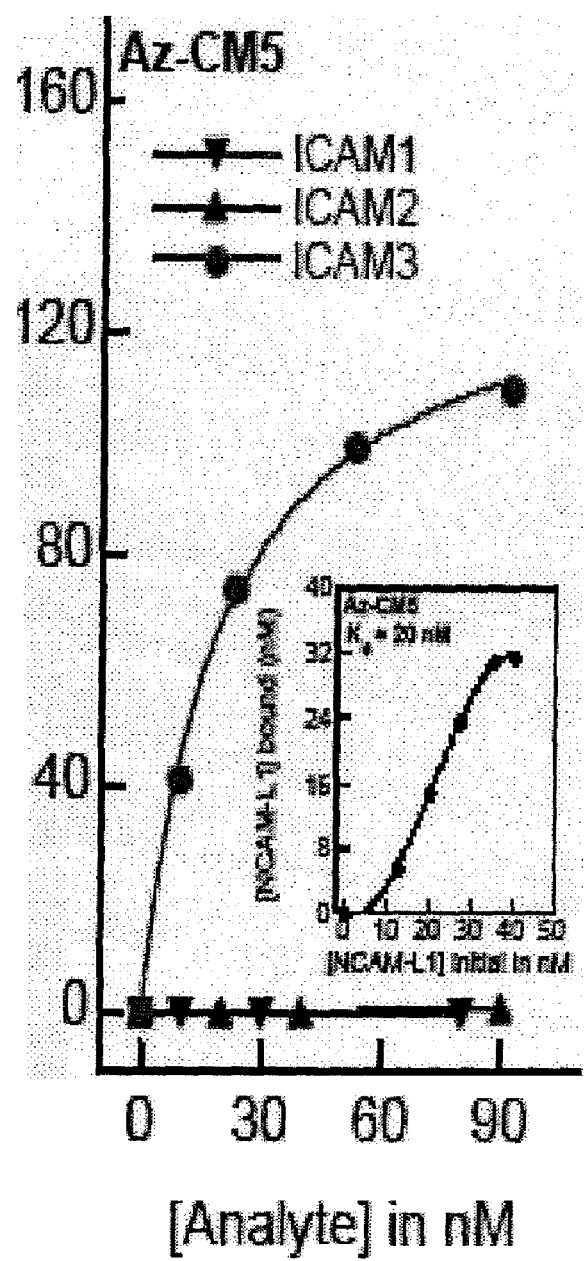

FIG. 3. FIG. 3 depicts surface plasmon resonance binding curves for the binding of ICAMs (ICAM-1, ICAM-2, ICAM-3 and NCAM, inset) with immobilized azurin. Due to large nonspecific binding to the bare Au-CM5 chip, CM5 was added as an eluent to the running buffer (1 mg/ml CM5 to HBS-EP buffer). The selective recognition of azurin with ICAM-3, but not with ICAM-1 or ICAM-2, is notable and the binding strength was 19.5±5.4 nM. The Kd for NCAM binding with azurin, as shown in the inset, was 20±5.0 nM.

BRIEF DESCRIPTION OF THE SEQUENCES

SEQ ID NO: 1 is the amino acid sequence of azurin from *Pseudomonas aeruginosa*.

SEQ ID NO: 2 is the amino acid sequence of cytochrome $c_{551}$ from *Pseudomonas aeruginosa*.

SEQ ID NO: 3 is the amino acid sequence of Laz from *Neisseria meningitidis* MC58.

SEQ ID NO: 4 is the amino acid sequence of plastocyanin from *Phormidium laminosum*.

SEQ ID NO: 5 is the amino acid sequence of rusticyanin from *Thiobacillus ferrooxidans* (*Acidithiobacillus ferrooxidans*).

SEQ ID NO: 6 is the amino acid sequence of pseudoazurin from *Achromobacter cycloclastes*.

SEQ ID NO: 7 is the amino acid sequence of azurin from *Alcaligenes faecalis*.

SEQ ID NO: 8 is the amino acid sequence of azurin from *Achromobacter xylosoxidans* ssp. *denitrificans* I.

SEQ ID NO: 9 is the amino acid sequence of azurin from *Bordetella bronchiseptica*.

SEQ ID NO: 10 is the amino acid sequence of azurin from *Methylomonas* sp. J.

SEQ ID NO: 11 is the amino acid sequence of azurin from *Neisseria meningitidis* Z2491.

SEQ ID NO: 12 is the amino acid sequence of azurin from *Pseudomonas fluorescens*.

SEQ ID NO: 13 is the amino acid sequence of azurin from *Pseudomonas chlororaphis*.

SEQ ID NO: 14 is the amino acid sequence of azurin from *Xylella fastidiosa* 9a5c.

SEQ ID NO: 15 is the amino acid sequence of stellacyanin from *Cucumis sativus*

SEQ ID NO: 16 is the amino acid sequence of auracyanin A from *Chloroflexus aurantiacus*

SEQ ID NO: 17 is the amino acid sequence of auracyanin B from *Chloroflexus aurantiacus*

SEQ ID NO: 18 is the amino acid sequence of cucumber basic protein from *Cucumis sativus*

SEQ ID NO: 19 is the amino acid sequence of cytochrome c from *Homo sapiens*.

SEQ ID NO: 20 is the amino acid sequence of cytochrome f from cyanobacteria *Phormidium laminosum*.

SEQ ID NO: 21 is the amino acid sequence of the H.8 region of Laz from *Neisseria gonorrhoeae* F62.

SEQ ID NO: 22 is the amino acid sequence of Laz from *Neisseria gonorrhoeae* F62.

SEQ ID NO: 23 is the forward primer to PCR amplify the Laz-encoding gene (laz) of *Neisseria gonorrhoeae*.

SEQ ID NO: 24 is the reverse primer to PCR amplify the Laz-encoding gene (laz) of *Neisseria gonorrhoeae*.

SEQ ID NO: 25 is the forward primer to PCR amplify a 3.1 kb fragment of pUC18-laz.

SEQ ID NO: 26 is the reverse primer to PCR amplify a 3.1 kb fragment of pUC18-laz.

SEQ ID NO: 27 is the forward primer to PCR amplify a 0.4 kb fragment of pUC19-paz.

SEQ ID NO: 28 is the reverse primer to PCR amplify a 0.4 kb fragment of pUC19-paz.

SEQ ID NO: 29 is the forward primer for pGST-azu 36-128.

SEQ ID NO: 30 is the reverse primer for pGST-azu 36-128.

SEQ ID NO: 31 is the forward primer for pGST-azu 36-89.

SEQ ID NO: 32 is the reverse primer for pGST-azu 36-89.

SEQ ID NO: 33 is the forward primer for pGST-azu 88-113.

SEQ ID NO: 34 is the reverse primer for pGST-azu 88-113.

SEQ ID NO: 35 is an oligonucleotide for site directed mutagenesis for the preparation of pGST-azu 88-113.

SEQ ID NO: 36 is an oligonucleotide for site directed mutagenesis for the preparation of pGST-azu 88-113.

DETAILED DESCRIPTION OF THE INVENTION

Definitions

As used herein, the term "cell" includes both the singular or the plural of the term, unless specifically described as a "single cell."

As used herein, the terms "polypeptide," "peptide," and "protein" are used interchangeably to refer to a polymer of amino acid residues. The terms apply to amino acid polymers in which one or more amino acid residue is an artificial chemical analogue of a corresponding naturally occurring amino acid. The terms also apply to naturally occurring amino acid polymers. The terms "polypeptide," "peptide," and "protein" are also inclusive of modifications including, but not limited to, glycosylation, lipid attachment, sulfation, gamma-carboxylation of glutamic acid residues, hydroxylation and ADP-ribosylation. It will be appreciated that polypeptides are not always entirely linear. For instance, polypeptides may be branched as a result of ubiquitination and they may be circular (with or without branching), generally as a result of post-translation events, including natural processing event and events brought about by human manipulation which do not occur naturally. Circular, branched and branched circular polypeptides may be synthesized by non-translation natural process and by entirely synthetic methods as well.

As used herein, the term "pathological condition" includes anatomic and physiological deviations from the normal that constitute an impairment of the normal state of the living animal or one of its parts, that interrupts or modifies the performance of the bodily functions, and is a response to various factors (as malnutrition, industrial hazards, or climate), to specific infective agents (as worms, parasitic protozoa, bacteria, or viruses), to inherent defects of the organism (as genetic anomalies), or to combinations of these factors.

As used herein, the term "condition" includes anatomic and physiological deviations from the normal that constitute an impairment of the normal state of the living animal or one of its parts, that interrupts or modifies the performance of the bodily functions.

As used herein, the term "suffering from" includes presently exhibiting the symptoms of a pathological condition, having a pathological condition even without observable symptoms, in recovery from a pathological condition, or recovered from a pathological condition.

As used herein, the term "parasitemia" includes a condition in which parasites are present in the blood and other tissues, and in particular to indicate the presence of parasites with or without clinical symptoms.

As used herein, the term "inhibition of parasitemia" refers to a decrease or a lessening of the rate of increase of the presence of the parasite in the blood of a mammal. Inhibition is any decrease or lessening of the rate of increase that is statistically significant as compared to control treatments.

A used herein, the term "treatment" includes preventing, lowering, stopping, or reversing the progression or severity of the condition or symptoms associated with a condition being treated. As such, the term "treatment" includes medical, therapeutic, and/or prophylactic administration, as appropriate.

As used herein, "anti-malarial activity" includes any activity that decreases the infectivity, the reproduction, or inhibits the progress of the lifecycle of a malaria parasite. "Anti-malarial activity" includes inhibition of the growth of malaria infection by all of the means of observed with current anti-malarial drugs.

As used herein, the term "anti-malarial drug" refers to drugs with anti-malarial activity that may be used to decrease the infectivity, the reproduction, or inhibit the progress of the lifecycle of a malaria parasite.

As used herein, the term "anti-HIV drug" refers to drugs with anti-HIV activity HIV by which HIV infection in mammals is decreased, or prevented from increasing in the human body, by any means including, but are not limited to, inhibition of replication of the HIV genome, inhibition of synthesis and/or assembly of the HIV coat proteins, and inhibition of HIV entry into uninfected cells.

The term "substantially pure", when used to modify the term a polypeptide or other compound, as used herein, refers to a polypeptide or compound, for example, a polypeptide isolated from the growth medium, in a form substantially free of, or unadulterated by, active inhibitory agents. The term "substantially pure" refers to a compound in an amount of at least about 75%, by dry weight, of isolated fraction, or "75% substantially pure." More specifically, the term "substantially pure" refers to a compound of at least about 85%, by dry weight, active compound, or "85% substantially pure." Most specifically, the term "substantially pure" refers to a compound of at least about 95%, by dry weight, active compound, or "95% substantially pure." The substantially pure cupredoxin or cytochrome $c_{551}$ or a variant or derivative thereof can be used in combination with one or more other substantially pure compounds, or another isolated cupredoxin or cytochrome.

The phrases "isolated," "purified" or "biologically pure" refer to material which is substantially or essentially free from components which normally accompany the material as it is found in its native state. Thus, isolated peptides in accordance with the invention preferably do not contain materials normally associated with the peptides in their in situ environment. An "isolated" region refers to a region that does not include the whole sequence of the polypeptide from which the region was derived. An "isolated" nucleic acid, protein, or respective fragment thereof has been substantially removed from its in vivo environment so that it may be manipulated by the skilled artisan, such as but not limited to nucleotide sequencing, restriction digestion, site-directed mutagenesis, and subcloning into expression vectors for a nucleic acid fragment as well as obtaining the protein or protein fragment in substantially pure quantities.

The term "variant" as used herein with respect to a peptide, refers to amino acid sequence variants which may have amino acids replaced, deleted, or inserted as compared to the wild-type polypeptide. Variants may be truncations of the wild-type peptide. Thus, a variant peptide may be made by manipulation of genes encoding the polypeptide. A variant may be made by altering the basic composition or characteristics of the polypeptide, but not at least some of its fundamental activities. For example, a "variant" of azurin can be a mutated azurin that retains its ability to inhibit parasitemia in malaria-infected human red blood cells. In some cases, a variant peptide is synthesized with non-natural amino acids, such as $\epsilon$-(3,5-dinitrobenzoyl)-Lys residues. (Ghadiri & Fernholz, J. Am. Chem. Soc., 112:9633-9635 (1990)) In some embodiments, the variant has not more than 20 amino acids replaced, deleted or inserted compared to wild-type peptide. In some embodiments, the variant has not more than 15, 14, 13, 12 or 11 amino acids replaced, deleted or inserted compared to wild-type peptide. In some embodiments, the variant has not more than 10, 9, 8 or 7 amino acids replaced, deleted or inserted compared to wild-type peptide. In some embodiments, the variant has not more than 6 amino acids replaced, deleted or inserted compared to wild-type peptide. In some embodiments, the variant has not more than 5 or 4 amino acids replaced, deleted or inserted compared to wild-type peptide. In some embodiments, the variant has not more than 3, 2 or 1 amino acids replaced, deleted or inserted compared to wild-type peptide.

The term "amino acid," as used herein, means an amino acid moiety that comprises any naturally-occurring or non-naturally occurring or synthetic amino acid residue, i.e., any moiety comprising at least one carboxyl and at least one amino residue directly linked by one, two three or more carbon atoms, typically one ($\alpha$) carbon atom.

The term "derivative" as used herein with respect to a peptide refers to a peptide that is derived from the subject peptide. A derivation includes chemical modifications of the peptide such that the peptide still retains some of its fundamental activities. For example, a "derivative" of azurin can be a chemically modified azurin that retains its ability to inhibit parasitemia in malaria-infected red blood cells. Chemical modifications of interest include, but are not limited to, amidation, acetylation, sulfation, polyethylene glycol (PEG) modification, phosphorylation or glycosylation of the peptide. In addition, a derivative peptide maybe a fusion of a polypeptide or fragment thereof to a chemical compound, such as but not limited to, another peptide, drug molecule or other therapeutic or pharmaceutical agent or a detectable probe.

The term "percent (%) amino acid sequence identity" is defined as the percentage of amino acid residues in a polypeptide that are identical with amino acid residues in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. In a specific embodiment, Blastp (available from the National Center for Biotechnology Information, Bethesda Md.) is used using the default parameters of long complexity filter, expect 10, word size 3, existence 11 and extension 1.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

% amino acid sequence identity=$X/Y*100$ where

X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A. When comparing longer sequences to shorter sequences, the shorter sequence will be the "B" sequence, unless stated otherwise. For example, when comparing truncated peptides to the corresponding wild-type polypeptide, the truncated peptide will be the "B" sequence.

A "therapeutically effective amount" is an amount effective to prevent or slow the development of, or to partially or totally alleviate the existing symptoms in a particular condition, pathological or otherwise, for which the subject being treated. Determination of a therapeutically effective amount is well within the capability of those skilled in the art.

General

The present invention provides compositions and methods that use cupredoxin and/or cytochrome to inhibit parasitemia of malaria-infected mammalian red blood cells and bodily tissues, such as brain tissue and bone tissue.

Previously it was known that several bacterial redox proteins belonging to a family of the blue copper-containing proteins called cupredoxins, or the iron (haem)-containing proteins called cytochromes, enter mammalian cells, including cancer cells, and either induce apoptotic cell death or cause growth inhibition through G1 arrest of the cell cycle. (Yamada et al., Cell Cycle 3:752-755 (2004); Yamada et al., Cell Cycle 3:1182-1187 (2004)) Single bacterial proteins such as the cupredoxin azurin or the cytochrome $c_{551}$, both elaborated by *Pseudomonas aeruginosa*, can demonstrate either activity based on their hydrophobicity. Thus wild type (wt) azurin induces apoptosis in the murine J774 cells (Yamada et al., Infection and Immunity 70:7054-7062 (2002)) while a mutant M44KM64E azurin causes cell cycle inhibition at the G1 phase in J774 cells. (Yamada et al., PNAS 101:4770-4775 (2004)) In contrast, wt cytochrome $C_{551}$ causes cell cycle inhibition at the G1 phase in J774 cells while a mutant V23DI59E cytochrome $c_{551}$ induces apoptosis. (Hiraoka et al., PNAS 101:6427-6432 (2004))

In accordance with the present invention, it is surprisingly now known that cupredoxins and cytochromes will inhibit in vitro parasitemia in human red blood cells by the malaria parasite *Plasmodium falciparum*. In particular, the cupre-doxins azurin and Laz inhibit parasitemia in *P. falciparum* by about 50% and about 75% respectively. See, Example 6. Further, rusticyanin and cytochromes c and f inhibited parasitemia by 20-30%. See, Example 1. Further, it is now known that azurin has a discernable structural homology to the Fab fragment of G17.12 mouse monoclonal antibody when complexed to the Pf MSP1-19 fragment of the MSP1 surface protein of *P. falciparum*. See, Example 2. While not limiting the mode of inhibition to any one means, it is thought that azurin may inhibit parasitemia of *P. falciparum* by interaction with the MSP1 protein on the parasite's surface.

Surprisingly, it is now known that azurin and Laz bind both the PfMSP1-19 and PfMSP1-42 *P. falciparum* surface proteins in vitro. Further, it is now known that azurin amino acid residues 36-89 are required for binding to PfMSP1-19 and PfMSP1-42. Further, it is now known that the H.8 domain of Laz from *N. gonorrhea* increases both the binding of a fused azurin to PfMSP1-19 as well as inhibition of parasitemia by *P. falciparum*. See, Examples 5 and 6.

Because of the high structural homology between the cupredoxins, it is contemplated that other cupredoxins will have the same anti-malarial activity as the azurin, rusticyanin, or Laz. In some embodiments, the cupredoxin is, but is not limited to, azurin, pseudoazurin, plastocyanin, auracyanin, Laz or rusticyanin. In specific embodiments, the cupredoxin is Laz, azurin or rusticyanin. In other embodiments, the cupredoxin is from a pathogenic bacteria. In a more specific embodiment, the cupredoxin is azurin. In particularly specific embodiments, the azurin is derived from *Pseudomonas aeruginosa, Alcaligenes faecalis, Achromobacter xylosoxidans* ssp. *denitrificans* I, *Bordetella bronchiseptica, Methylomonas* sp., *Neisseria meningitidis* Z2491, *Pseudomonas fluorescens, Pseudomonas chlororaphis, Xylella fastidiosa* 9a5 or *Vibrio parahaemolyticus*. In a most specific embodiment, the azurin is from *P. aeruginosa*. In other specific embodiments, the cupredoxin comprises an amino acid sequence that is SEQ ID NO:1, 2-18 or 21.

In accordance with the present invention, it has been learned that *P. aeruginosa* cytochrome $c_{551}$, human cytochrome c and *Phormidium laminosum* cytochrome f will inhibit parasitemia in malaria-infected human red blood cells. In a specific embodiment, the cytochrome is cytochrome $c_{551}$ from *P. aeruginosa*, human cytochrome c or cytochrome f. In other specific embodiments, the cytochrome comprises an amino acid sequence that is SEQ ID NO: 2, 19 or 20.

Because of the structural homology between the cytochrome c's, it is contemplated that other cytochromes will have the same anti-malarial activity as *P. aeruginosa* cytochrome $c_{551}$ and human cytochrome c. In some embodiments, the cytochrome is from a pathogenic bacterium. In another specific embodiment, the cytochrome inhibits parasitism in malaria-infected red blood cells, and more specifically, human red blood cells. In another specific embodiment, the cytochrome inhibits cell cycle progression in a mammalian cancer cell, and more specifically in a J774 cell.

Compositions of the Invention

The invention provides for peptides that are variants, derivatives or structural equivalents of cupredoxin or cytochrome. In some embodiments, the peptide is substantially pure. In other embodiments, the peptide is isolated. In some embodiments, the peptide is less that a full length cupredoxin or cytochrome, and retains some of the functional characteristics of the cupredoxin or cytochrome. In some embodiments, the peptide retains the ability to inhibit parasitemia in malaria-infected red blood cells, and more specifically the ability to inhibit *P. falciparum* infection in human red blood cells. In specific embodiments, the cytochrome is *P. aeruginosa* cytochrome $c_{551}$, human cytochrome c, or cyanobacterial cytochrome f, and specifically SEQ ID NOS: 2, 19, and 20. In another specific embodiment, the peptide does not raise an immune response in a mammal, and more specifically a human.

The invention also provides compositions comprising at least one peptide that is a cupredoxin, cytochrome, or variant, derivative or structural equivalent of a cupredoxin or cytochrome. The invention also provides compositions comprising at least one peptide that is a cupredoxin or variant, derivative or structural equivalent of a cupredoxin. The invention also provides compositions comprising at least one peptide that is a cytochrome, or variant, derivative or structural equivalent of a cytochrome. In other embodiments, the composition consists essentially of the peptide. The invention also provides compositions comprising at least one peptide that is a cupredoxin, cytochrome, or variant, derivative or structural equivalent of a cupredoxin or cytochrome in a pharmaceutical composition.

Because of the high structural homology between the cupredoxins, it is contemplated that other cupredoxins will have the same anti-malarial activity as *Pseudomonas aeruginosa* azurin with regards to inhibition of parasitemia in malaria-infected red blood cells. In some embodiments, the cupredoxin is, but is not limited to, azurin, pseudoazurin, plastocyanin, rusticyanin, Laz or auracyanin. In particularly specific embodiments, the cupredoxin is derived from *Pseudomonas aeruginosa, Alcaligenes faecalis, Achromobacter xylosoxidans* ssp. *denitrificans* I, *Bordetella bronchiseptica, Methylomonas* sp., *Neisseria meningitidis* Z2491, *Neisseria gonorrhea, Pseudomonas fluorescens, Pseudomonas chlororaphis, Xylella fastidiosa* 9a5 or *Vibrio parahaemolyticus*. In a very specific embodiment, the cupredoxin is azurin from *Pseudomonas aeruginosa*. In other specific embodiments, the cupredoxin comprises an amino acid sequence that is SEQ ID NO: 1, 3-18, or 22. In other specific embodiments, the cupredoxin is the Laz protein from *Neisseria meningitidis* or *Neisseria gonorrhea*.

The invention provides for amino acid sequence variants of a cupredoxin or cytochrome which have amino acids replaced, deleted, or inserted as compared to the wild-type polypeptide. Variants of the invention may be truncations of the wild-type polypeptide. In some embodiments, the composition comprises a peptide that consists of a region of a cupredoxin or cytochrome that is less that the full length wild-type polypeptide. In some embodiments, the composition comprises a peptide that consists of more than about 10 residues, more than about 15 residues or more than about 20 residues of a truncated cupredoxin or cytochrome. In some embodiments, the composition comprises a peptide that consists of not more than about 100 residues, not more than about 50 residues, not more than about 40 residues or not more than about 30 residues of a truncated cupredoxin or cytochrome. In some embodiments, composition comprises a peptide to which a cupredoxin or cytochrome, and more specifically to SEQ ID NOS: 1-20 or 22 has at least about 90% amino acid sequence identity, at least about 95% amino acid sequence identity or at least about 99% amino acid sequence identity.

In specific embodiments, the variant of cupredoxin comprises *P. aeruginosa* azurin residues 36-89. In other embodiments, the variant of cupredoxin consists of *P. aeruginosa* azurin residues 36-89. In other specific embodiments, the variant consists of the equivalent residues of a cupredoxin other that azurin.

It is contemplated that other cupredoxin variants can be designed that have a similar activity to azurin residues 36-89. To do this, the subject cupredoxin amino acid sequence will be aligned to the *Pseudomonas aeruginosa* azurin sequence using BLAST, BLAST2, ALIGN2 or Megalign (DNASTAR), the relevant residues located on the *P. aeruginosa* azurin amino acid sequence, and the equivalent residues found on the subject cupredoxin sequence, and the equivalent residues of the cupredoxin thus identified.

The variants also include peptides made with synthetic amino acids not naturally occurring. For example, non-naturally occurring amino acids may be integrated into the variant peptide to extend or optimize the half-life of the composition in the bloodstream. Such variants include, but are not limited to, D,L-peptides (diastereomer), (Futaki et al., J. Biol. Chem. 276(8):5836-40 (2001); Papo et al., Cancer Res. 64(16):5779-86 (2004); Miller et al, Biochem. Pharmacol. 36(1): 169-76, (1987)); peptides containing unusual amino acids (Lee et al., J. Pept. Res. 63(2):69-84 (2004)), and incorporation of olefin-containing non-natural amino acid followed by hydrocarbon stapling (Schafmeister et al., J. Am. Chem. Soc. 122:5891-5892 (2000); Walenski et al., Science 305:1466-1470 (2004)) and peptides comprising ε-(3,5-dinitrobenzoyl)-Lys residues.

In other embodiments, the peptide of the invention is a derivative of a cupredoxin or cytochrome. The derivatives of cupredoxin or cytochrome are chemical modifications of the peptide such that the peptide still retains some of its fundamental activities. For example, a "derivative" of azurin can be a chemically modified azurin that retains its ability to inhibit the malaria parasitemia in mammalian cells. Chemical modifications of interest include, but are not limited to, amidation, acetylation, sulfation, polyethylene glycol (PEG) modification, phosphorylation and glycosylation of the peptide. In addition, a derivative peptide maybe a fusion of a cupredoxin or cytochrome, or variant, derivative or structural equivalent thereof to a chemical compound, such as but not limited to, another peptide, drug molecule or other therapeutic or pharmaceutical agent or a detectable probe. Derivatives of interest include chemical modifications by which the half-life in the bloodstream of the peptides and compositions of the invention can be extended or optimized, such as by several methods well known to those in the art, including but not limited to, circularized peptides (Monk et al., BioDrugs 19(4):261-78, (2005); DeFreest et al., J. Pept. Res. 63(5):409-19 (2004)), N- and C-terminal modifications (Labrie et al., Clin. Invest. Med. 13(5):275-8, (1990)), and incorporation of olefin-containing non-natural amino acid followed by hydrocarbon stapling (Schafmeister et al., J. Am. Chem. Soc. 122:5891-5892 (2000); Walenski et al., Science 305:1466-1470 (2004)).

In one embodiment, the cupredoxin or cytochrome, or variant, derivative or structural equivalent thereof, is fused to a H.8 region of Laz from *Neisseria meningitidis* or *Neisseria gonorrhea*. One example of such a peptide is the H.8-Paz fusion protein described in Example 4. In a specific embodiment, the H.8 is fused to the C-terminus of the cupredoxin or cytochrome, or variant, derivative or structural equivalent thereof. In another specific embodiment, the H.8 region is SEQ ID NO: 21, or a variant, derivative or structural equivalent thereof.

It is contemplated that the peptide of the composition of invention may be more than one of a variant, derivative and structural equivalent of a cupredoxin or cytochrome. For example, the peptide may be a truncation of azurin that has been PEGylated, thus making it both a variant and a derivative. In one embodiment, the peptides of the invention are synthesized with α,α-disubstituted non-natural amino acids containing olefin-bearing tethers, followed by an all-hydrocarbon "staple" by ruthenium catalyzed olefin metathesis. (Scharmeister et al., J. Am. Chem. Soc. 122:5891-5892 (2000); Walensky et al., Science 305:1466-1470 (2004)) Additionally, peptides that are structural equivalents of azurin may be fused to other peptides, thus making a peptide that is both a structural equivalent and a derivative. These examples are merely to illustrate and not to limit the invention. Variants, derivatives or structural equivalents of cupredoxin or cytochrome may or may not bind copper.

In another embodiment, the peptide may be a structural equivalent of a cupredoxin or cytochrome. Examples of studies that determine significant structural homology between cupredoxins and cytochromes and other proteins include Toth et al. (*Developmental Cell* 1:82-92 (2001)). Specifically, significant structural homology between a cupredoxin or cytochrome and its structural equivalents are determined by using the VAST algorithm (Gibrat et al., Curr Opin Struct Biol 6:377-385 (1996); .Madej et al., Proteins 23:356-3690 (1995)). In specific embodiments, the VAST p value from a structural comparison of a cupredoxin or cytochrome to the structural equivalent is less than about $10^{-3}$, less than about $10^{-5}$, or less than about $10^{-7}$. In other embodiments, significant structural homology between a cupredoxin or cytochrome and its structural equivalents are determined by using the DALI algorithm (Holm & Sander, J. Mol. Biol. 233:123-138 (1993)). In specific embodiments, the DALI Z score for a pairwise structural comparison is at least about 3.5, at least about 7.0, or at least about 10.0.

In another embodiment, the variant or derivative of cupredoxin has a significant structural homology to the Fab fragment of G17.12 mouse monoclonal antibody. An example of how this structural similarity can be determined can be found in Example 3. Specifically, significant structural homology between a cupredoxin and the Fab fragment of G17.12 mouse monoclonal antibody can be determined by using the VAST algorithm (Gibrat et al., id.; Madej et al., id.). In specific embodiments, the VAST p-value from a structural comparison of a cupredoxin to the Fab fragment of G17.12 mouse monoclonal antibody can be less than about $10^{-4}$, less than about $10^{-5}$, less than about $10^{-6}$, or less than about $10^{-7}$. In other specific embodiments, the VAST score from a structural comparison of a cupredoxin to the Fab fragment of G17.12 mouse monoclonal antibody can be greater than about 9, greater than about 10, greater than about 11 or greater than about 12.

In some embodiments, the variant, derivative or structural equivalent thereof has some of the functional characteristics of the *P. aeruginosa* azurin, *P. aeruginosa* cytochrome $c_{551}$, human cytochrome c or cyanobacterial cytochrome f. In a specific embodiment, the peptide of the invention inhibits parasitemia by malaria in malaria-infected red blood cells, and more specifically parasitemia by *P. falciparum* in *P. falciparum*-infected human red blood cells. The invention also provides for the variants, derivatives and structural equivalents of cupredoxin and cytochrome $c_{551}$ that retain the ability to inhibit parasitemia in malaria-infected red blood cells, and more specifically parasitemia by *P. falciparum* in *P. falciparum*-infected human red blood cells. The inhibition of parasitemia by *P. falciparum* in *P. falciparum*-infected human red blood cells may be determined by the method described in Example 6.

Because it is now known that cupredoxins and cytochrome can inhibit parasitemia in malaria-infected red blood cells, it is now possible to design variants, derivatives and structural equivalents of cupredoxins and cytochrome that retain this anti-malarial activity. Such variants and derivatives can be made by, for example, creating a "library" of various variants and derivatives of cupredoxins and cytochromes, and then testing each for anti-malarial activity using one of many methods known in the art, such the exemplary method in Example 6. It is contemplated that the resulting variants, derivatives and structural equivalents of cupredoxins and cytochromes with anti-malarial activity can be used in the methods of the invention, in place of or in addition to the cupredoxins and cytochromes mentioned herein. This method of selecting variants and derivatives may be adapted for any of the activities of *P. aeruginosa* azurin, *P. aeruginosa* cytochrome $c_{551}$, human cytochrome c or cyanobacterial cytochrome f disclosed herein.

In other embodiments, the peptide of the invention inhibits intracellular replication of the malaria parasite in human red blood cells. Methods to determine the intracellular replication of the malaria parasite are well known in the art, and one such method is described in Example 2.

In some embodiments, the peptide of the invention binds to the PfMSP1-19 and/or PfMSP1-42 *P. falciparum* surface proteins with a relative binding affinity that is statistically greater a non-binding control protein. A peptide can be tested for this activity by using surface plasmon resonance analysis as described in Example 5. Other methods to determine whether one protein binds to another are well known in the art and may be used as well.

In another embodiment, the peptide of the invention binds to ICAM-3 or NCAM with a relative binding affinity that is statistically greater a non-binding control protein. A peptide can be tested for this activity by using surface plasmon resonance analysis as described in Examples 7 and 5. Other methods to determine whether one protein binds to another are well known in the art and may be used as well.

In some specific embodiments, the peptides of the invention induce apoptosis in a mammalian cancer cell, more specifically a J774 cell. The ability of a peptide to induce apoptosis may be observed by mitosensor ApoAlert™ confocal microscopy using a MITOSENSOR™ APOLERT™ Mitochondrial Membrane Sensor kit (Clontech Laboratories, Inc., Palo Alto, Calif., U.S.A.), by measuring caspase-8, caspase-9 and caspase-3 activity using the method described in Zou et al. (*J. Biol. Chem*. 274: 11549-11556 (1999)), and by detecting apoptosis-induced nuclear DNA fragmentation using, for example, the APOLERT™ DNA fragmentation kit (Clontech Laboratories, Inc., Palo Alto, Calif., U.S.A.).

In another specific embodiment, the peptide of the invention induces cellular growth arrest in a mammalian cancer cell, more specifically a J774 cell. Cellular growth arrest can be determined by measuring the extent of inhibition of cell cycle progression, such as by the method found in Yamada et al. (*PNAS* 101:4770-4775 (2004)). In another specific embodiment, the peptide of the invention inhibits cell cycle progression in a mammalian cancer cell, more specifically a J774 cell.

Cupredoxins

These small blue copper proteins (cupredoxins) are electron transfer proteins (10-20 kDa) that participate in bacterial electron transfer chains or are of unknown function. The copper ion is solely bound by the protein matrix. A special distorted trigonal planar arrangement to two histidine and one cysteine ligands around the copper gives rise to very peculiar electronic properties of the metal site and an intense blue color. A number of cupredoxins have been crystallographically characterized at medium to high resolution.

The cupredoxins in general have a low sequence homology but high structural homology. (Gough & Clothia, *Structure* 12:917-925 (2004); De Rienzo et al., *Protein Science* 9:1439-1454 (2000).) For example, the amino acid sequence of azurin is 31% identical to that of auracyanin B, 16.3% to that of rusticyanin, 20.3% to that of plastocyanin, and 17.3% to that of pseudoazurin. See Table 1. However, the structural similarity of these proteins is more pronounced. The VAST p value for the comparison of the structure of azurin to auracyanin B is $10^{-7.4}$, azurin to rusticyanin is $10^{-5}$, azurin to plastocyanin is $10^{-5.6}$, and azurin to psuedoazurin is $10^{-4.1}$.

All of the cupredoxins possess an eight-stranded Greek key beta-barrel or beta-sandwich fold and have a highly conserved site architecture. (De Rienzo et al., *Protein Science* 9:1439-1454 (2000).) A prominent hydrophobic patch, due to the presence of many long chain aliphatic residues such as methionines and leucines, is present around the copper site in azurins, amicyanins, cyanobacterial plastocyanins, cucumber basic protein and to a lesser extent, pseudoazurin and eukaryotic plastocyanins. Id. Hydrophobic patches are also found to a lesser extent in stellacyanin and rusticyanin copper sites, but have different features. Id.

TABLE 1

Sequence and structure alignment of azurin (1JZG) from
*P. aeruginosa* to other proteins using VAST algorithm.

| PDB | Alignment length[1] | % aa identity | P-value[2] | Score[3] | RMSD[4] | Description |
|---|---|---|---|---|---|---|
| 1AOZ A 2 | 82 | 18.3 | 10e−7 | 12.2 | 1.9 | Ascorbate oxidase |
| 1QHQ_A | 113 | 31 | 10e−7.4 | 12.1 | 1.9 | AuracyaninB |
| 1V54 B 1 | 79 | 20.3 | 10e−6.0 | 11.2 | 2.1 | Cytochrome c oxidase |
| 1GY2 A | 92 | 16.3 | 10e−5.0 | 11.1 | 1.8 | Rusticyanin |
| 3MSP A | 74 | 8.1 | 10e−6.7 | 10.9 | 2.5 | Motile Major Sperm Protein[5] |
| 1IUZ | 74 | 20.3 | 10e−5.6 | 10.3 | 2.3 | Plastocyanin |
| 1KGY E | 90 | 5.6 | 10e−4.6 | 10.1 | 3.4 | Ephrinb2 |
| 1PMY | 75 | 17.3 | 10e−4.1 | 9.8 | 2.3 | Pseudoazurin |

[1]Aligned Length: The number of equivalent pairs of C-alpha atoms superimposed between the two structures, i.e. how many residues have been used to calculate the 3D superposition.
[2]P-VAL: The VAST p value is a measure of the significance of the comparison, expressed as a probability. For example, if the p value is 0.001, then the odds are 1000 to 1 against seeing a match of this quality by pure chance. The p value from VAST is adjusted for theeffects of multiple comparisons using the assumption that there are 500 independent and unrelated types of domains in the MMDB database. The p value shown thus corresponds to the p value for the pairwise comparison of each domain pair, divided by 500.
[3]Score: The VAST structure-similarity score. This number is related to the number of secondary structure elements superimposed and the quality of that superposition. Higher VAST scores correlate with higher similarity.
[4]RMSD: The root mean square superposition residual in Angstroms. This number is calculated after optimal superposition of two structures, as the square root of the mean square distances between equivalent C-alpha atoms. Note that the RMSD value scales with the extentof the structural alignments and that this size must be taken into consideration when using RMSD as a descriptor of overall structural similarity.
[5]*C. elegans* major sperm protein proved to be an ephrin antagonist in oocyte maturation (Kuwabara, 2003 "The multifaceted *C. elegans* major sperm protein: an ephrin signalling antagonist in oocyte maturation" Genes and Development, 17: 155-161.

Azurin

The azurins are copper containing proteins of 128 amino acid residues which belong to the family of cupredoxins involved in electron transfer in plants and certain bacteria. The azurins include those from *P. aeruginosa* (PA) (SEQ ID NO: 1), *A. xylosoxidans*, and *A. denitrificans* (SEQ ID NO: 8). (Murphy et al., *J. Mol. Biol*. 315:859-871 (2002)) The amino acid sequence identity between the azurins varies between 60-90%, these proteins showed a strong structural homology. All azurins have a characteristic β-sandwich with Greek key motif and the single copper atom is always placed at the same region of the protein. In addition, azurins possess an essentially neutral hydrophobic patch surrounding the copper site. Id.

Plastocyanins

The plastocyanins are soluble proteins of cyanobacteria, algae and plants that contain one molecule of copper per molecule and are blue in their oxidized form. They occur in the chloroplast, where they function as electron carriers. Since the determination of the structure of poplar plastocyanin in 1978, the structure of algal (*Scenedesmus, Enteromorpha, Chlamydomonas*) and plant (French bean) plastocyanins has been determined either by crystallographic or NMR methods, and the poplar structure has been refined to 1.33 Å resolution. SEQ ID NO: 4 shows the amino acid sequence of plastocyanin from *Phormidium laminosum*, a thermophilic cyanobacterium.

Despite the sequence divergence among plastocyanins of algae and vascular plants (e.g., 62% sequence identity between the *Chlamydomonas* and poplar proteins), the three-dimensional structures are conserved (e.g., 0.76 Å rms deviation in the C alpha positions between the *Chlamydomonas* and *Poplar* proteins). Structural features include a distorted tetrahedral copper binding site at one end of an eight-stranded antiparallel beta-barrel, a pronounced negative patch, and a flat hydrophobic surface. The copper site is optimized for its electron transfer function, and the negative and hydrophobic patches are proposed to be involved in recognition of physiological reaction partners. Chemical modification, cross-linking, and site-directed mutagenesis experiments have confirmed the importance of the negative and hydrophobic patches in binding interactions with cytochrome f, and validated the model of two functionally significant electron transfer paths involving plastocyanin. One putative electron transfer path is relatively short (approximately 4 Å) and involves the solvent-exposed copper ligand His-87 in the hydrophobic patch, while the other is more lengthy (approximately 12-15 Å) and involves the nearly conserved residue Tyr-83 in the negative patch, Redinbo et al., *J. Bioenerg. Biomembr*. 26:49-66 (1994).

Rusticyanins

Rusticyanins are blue-copper containing single-chain polypeptides obtained from a Thiobacillus (now called Acidithiobacillus). The X-ray crystal structure of the oxidized form of the extremely stable and highly oxidizing cupredoxin rusticyanin from *Thiobacillus ferrooxidans* (SEQ ID NO: 5) has been determined by multiwavelength anomalous diffraction and refined to 1.9 Å resolution. The rusticyanins are composed of a core beta-sandwich fold composed of a six- and a seven-stranded b-sheet. Like other cupredoxins, the copper ion is coordinated by a cluster of four conserved residues (His 85, Cys138, His143, Met148) arranged in a distorted tetrahedron. Walter, R. L. et al., J. Mol. Biol., vol. 263, pp-730-51 (1996).

Pseudoazurins

The pseudoazurins are a family of blue-copper containing single-chain polypeptide. The amino acid sequence of pseudoazurin obtained from *Achromobacter cycloclastes* is shown in SEQ ID NO: 6. The X-ray structure analysis of pseudoazurin shows that it has a similar structure to the azurins although there is low sequence homology between these proteins. Two main differences exist between the overall structure of the pseudoazurins and azurins. There is a carboxy terminus extension in the pseudoazurins, relative to the azurins, consisting of two alpha-helices. In the mid-peptide region azurins contain an extended loop, shortened in the pseudoazurins, which forms a flap containing a short α-helix. The only major differences at the copper atom site are the conformation of the MET side-chain and the Met-S copper bond length, which is significantly shorter in pseudoazurin than in azurin.

Phytocyanins

The proteins identifiable as phytocyanins include, but are not limited to, cucumber basic protein, stellacyanin, mavicyanin, umecyanin, a cucumber peeling cupredoxin, a putative blue copper protein in pea pods, and a blue copper protein from *Arabidopsis thaliana*. In all except cucumber basic protein and the pea-pod protein, the axial methionine ligand normally found at blue copper sites is replaced by glutamine.

Auracyanin

Three small blue copper proteins designated auracyanin A, auracyanin B-1, and auracyanin B-2 have been isolated from the thermophilic green gliding photosynthetic bacterium *Chloroflexus aurantiacus*. The two B forms are glycoproteins and have almost identical properties to each other, but are distinct from the A form. The sodium dodecyl sulfate-polyacrylamide gel electrophoresis demonstrates apparent monomer molecular masses as 14 (A), 18 (B-2), and 22 (B-1) kDa.

The amino acid sequence of auracyanin A has been determined and showed auracyanin A to be a polypeptide of 139 residues. (Van Dreissche et al., Protein Science 8:947-957 (1999).) His58, Cys123, His128, and Met132 are spaced in a way to be expected if they are the evolutionary conserved metal ligands as in the known small copper proteins plastocyanin and azurin. Secondary structure prediction also indicates that auracyanin has a general beta-barrel structure similar to that of azurin from *Pseudomonas aeruginosa* and plastocyanin from poplar leaves. However, auracyanin appears to have sequence characteristics of both small copper protein sequence classes. The overall similarity with a consensus sequence of azurin is roughly the same as that with a consensus sequence of plastocyanin, namely 30.5%. The N-terminal sequence region 1-18 of auracyanin is remarkably rich in glycine and hydroxy amino acids. Id. See exemplary amino acid sequence SEQ ID NO: 16 for chain A of auracyanin from *Chloroflexus aurantiacus* (NCBI Protein Data Bank Accession No. AAM12874).

The auracyanin B molecule has a standard cupredoxin fold. The crystal structure of auracyanin B from *Chloroflexus aurantiacus* has been studied. (Bond et al., *J. Mol. Biol.* 306:47-67 (2001).) With the exception of an additional N-terminal strand, the molecule is very similar to that of the bacterial cupredoxin, azurin. As in other cupredoxins, one of the Cu ligands lies on strand 4 of the polypeptide, and the other three lie along a large loop between strands 7 and 8. The Cu site geometry is discussed with reference to the amino acid spacing between the latter three ligands. The crystallographically characterized Cu-binding domain of auracyanin B is probably tethered to the periplasmic side of the cytoplasmic membrane by an N-terminal tail that exhibits significant sequence identity with known tethers in several other membrane-associated electron-transfer proteins. The amino acid sequences of the B forms are presented in McManus et al. (*J. Biol. Chem.* 267:6531-6540 (1992).). See exemplary amino acid sequence SEQ ID NO: 17 for chain B of auracyanin from *Chloroflexus aurantiacus* (NCBI Protein Data Bank Accession No. 1QHQA).

Stellacyanin

Stellacyanins are a subclass of phytocyanins, a ubiquitous family of plant cupredoxins. An exemplary sequence of a stellacyanin is included herein as SEQ ID NO: 15. The crystal structure of umecyanin, a stellacyanin from horseradish root (Koch et al., J. Am. Chem. Soc. 127:158-166 (2005)) and cucumber stellacyanin (Hart et al., Protein Science 5:2175-2183 (1996).). The protein has an overall fold similar to the other phytocyanins. The ephrin B2 protein ectodomain tertiary structure bears a significant similarity to stellacyanin. (Toth et al., *Developmental Cell* 1:83-92 (2001).) An exemplary amino acid sequence of a stellacyanin is found in the National Center for Biotechnology Information Protein Data Bank as Accession No. 1JER, SEQ ID NO: 15.

Cucumber Basic Protein

An exemplary amino acid sequence from a cucumber basic protein is included herein as SEQ ID NO: 18. The crystal structure of the cucumber basic protein (CBP), a type 1 blue copper protein, has been refined at 1.8 Å resolution. The molecule resembles other blue copper proteins in having a Greek key beta-barrel structure, except that the barrel is open on one side and is better described as a "beta-sandwich" or "beta-taco". (Guss et al., *J. Mol. Biol.* 262: 686-705 (1996).) The ephrinB2 protein ectodomian tertiary structure bears a high similarity (rms deviation 1.5 Å for the 50 α carbons) to the cucumber basic protein. (Toth et al., *Developmental Cell* 1:83-92 (2001).)

The Cu atom has the normal blue copper NNSS' co-ordination with bond lengths Cu—N(His39)=1.93 A, Cu—S (Cys79)=2.16 A, Cu—N(His84)=1.95 A, Cu—S(Met89) =2.61 A. A disulphide link, (Cys52)-S—S-(Cys85), appears to play an important role in stabilizing the molecular structure. The polypeptide fold is typical of a sub-family of blue copper proteins (phytocyanins) as well as a non-metalloprotein, ragweed allergen Ra3, with which CBP has a high degree of sequence identity. The proteins currently identifiable as phytocyanins are CBP, stellacyanin, mavicyanin, umecyanin, a cucumber peeling cupredoxin, a putative blue copper protein in pea pods, and a blue copper protein from *Arabidopsis thaliana*. In all except CBP and the pea-pod protein, the axial methionine ligand normally found at blue copper sites is replaced by glutamine. An exemplary sequence for cucumber basic protein is found in NCBI Protein Data Bank Accession No. 2CBP, SEQ ID NO: 18.

Cytochromes

Cytochrome $C_{551}$

Cytochrome $C_{551}$ from *P. aeruginosa* (Pa-C551) is a monomeric redox protein of 82 amino-acid residues (SEQ ID NO: 2), involved in dissimilative denitrification as the physiological electron donor of nitrite reductase. The functional properties of Pa-C551 have been extensively investigated. The reactions with non-physiological small inorganic redox reactants and with other macromolecules, like blue copper proteins, eukaryotic cytochrome c and the physiological partner nitrite reductase have provided a test for protein-protein electron transfer.

The three-dimensional structure of Pa-C551, which is a member of bacterial class I cytochromes, shows a single low-spin heme with His-Met ligation and the typical polypeptide fold which however leaves the edges of pyrrole rings II and III of the heme exposed (Cutruzzola et al., *J. Inorgan. Chem.* 88:353-61 (2002)). The lack of a 20-residue omega loop, present in the mammalian class I cytochromes, causes further exposure of the heme edge at the level of propionate 13. The distribution of charged residues on the surface of Pa-C551 is very anisotropic: one side is richer in acidic residues whereas the other displays a ring of positive side chains, mainly lysines, located at the border of a hydrophobic patch which surrounds the heme crevice. This patch comprises residues Gly11, Val13, Ala14, Met22, Val23, Pro58, Ile59, Pro60, Pro62, Pro63 and Ala65. The anisotropic charge distribution leads to a large dipolar moment which is important for electron transfer complex formation.

The charge distribution described above for Pa-C551 has been reported for other electron transfer proteins and their electron acceptors. Moreover, modification by site-directed mutagenesis of residues within the hydrophobic or charged patch has shown for different proteins the importance of surface complementarity for binding and electron transfer. As an example, evidence for the relevance of the hydrophobic patch for the electron transfer properties of azurin from *P. aeruginosa* came from the studies carried out on mutants of residues Met44 and Met64 changed to positively and negatively charged amino acids. Id.

The cytochrome c-type domain has a fold consisting of a series of alpha helices and reverse turns that serve to envelop the covalently bound haem within a hydrophobic pocket. This domain can be found in monodomain cytochrome c proteins, such as cytochrome c6, cytochrome $c_{552}$, cytochrome $c_{459}$ and mitochondrial cytochrome c. The cytochrome c-type domain occurs in a number of other proteins, such as in cytochrome cd1-nitrite reductase as the N-terminal haem c domain, in quinoprotein alcohol dehydrogenase as the C-terminal domain, in Quinohemoprotein amine dehydrogenase A chain as domains 1 and 2, and in the cytochrome $bc_1$ complex as the cytochrome $bc_1$ domain. Structural analysis with VAST algorithm (cytochrome $C_{551}$ from *Pseudomonas aeruginosa* as a query) showed significant structural neighbors (P values between $10^{-10.3}$ to $10^{-4.5}$) only for cytochromes.

Methods of Use

The invention provides methods to treat patients with a malarial infection or at danger of acquiring one, or inhibit the spread of the malaria parasite. These methods comprise administering to a patient or an insect vector a cupredoxin or cytochrome, or variant, derivative or structural equivalent thereof which inhibits parasitemia of malaria-infected mammalian cells. The inhibition of parasitemia can be determined by many methods well known in the art. One method is described in Example 6, and determines the inhibition of parasitemia in malaria-infected human red blood cells. In other embodiments, the cupredoxin or cytochrome, or variant, derivative or structural equivalent thereof inhibits intracellular replication of the malaria parasite in human red blood cells and is administered to the patient or insect vector. Methods to determine the intracellular replication of the malaria parasite are well known in the art, and one such method is described in Example 2. The mode of the invention is not limited to any particular mechanism, and inhibition of parasitemia may result from many factors, including but not limited to, inhibition of replication of the parasite in infected blood cells, inhibition of parasite infecting uninfected blood cells, inhibition in the growth cycle of the parasite and inhibition of parasite entry into the mammalian cell.

The invention provides methods to treat patients suffering from infection by a malaria parasite by administering an effective amount of at least one protein that is a cupredoxin or cytochrome, or variant, derivative or structural equivalent thereof. The patients that may be treated by this method are any mammal that can be infected by a malaria parasite, and specifically are human patients. Malaria parasites known to infect mammals include, but are not limited to, *Plasmodium falciparum, P. vivax, P. berghei* (rodent-specific), *P. yoelli* (murine-specific), *P. cynomolgi* and *P. knowlesi* (monkey-specific).

It has also been learned that cupredoxins and cytochrome C551 are also effective against HIV-1 infections, as disclosed in a co-filed application. "Compositions And Methods For Treating HIV Infection With Cupredoxin And Cytochrome c," U.S. Provisional Patent Application Ser. No. 11/436,591, whose disclosure is expressly incorporated herein by reference. Further, co-infections with HIV and malaria are very common in many areas of the world, and in particular sub-Saharan Africa. In some embodiments, the patient suffering from infection by a malaria parasite is also suffering from infection by HIV. In some embodiments, the method of treatment of the invention also comprises administering anti-HIV drugs. In some embodiments, the anti-HIV drugs are co-administered.

The invention also provides methods to treat a patient suspected of having contact with a malaria parasite by administering an effective amount of at least one peptide that is a cupredoxin and/or a cytochrome, or a variant, derivative or structural equivalent of a cupredoxin or a cytochrome. A patient can be suspected of having contact with a malaria parasite, for example, if that patient lives or has traveled in a region of the world where malaria infection of others of the patient's species is common. Treatment by this method may be commenced when the patient is about to, or has already, come into contact with the malaria parasite. Contact with malaria parasites most often occurs by contact with an insect vector such as mosquitoes, so that areas abundant in these insects and the malaria parasite are considered to be among the areas where a patient would have a high probability of coming in contact with a malaria parasite. Such areas of the world include, but are not limited to, parts of Africa, Asia and Latin America. Further, a patient can be suspected of having contact with the malaria parasite if they have come into contact with blood infected with a malaria parasite, are intentionally exposed to the malaria parasite, or accidentally injected with blood or drugs contaminated with the parasite.

The cupredoxin or cytochrome, or variant, derivative or structural equivalent of cupredoxin or cytochrome can be administered to the patient by many routes and in many regimens that will be well known to those in the art. In specific embodiments, the cupredoxin or cytochrome, or variant, derivative or structural equivalent of cupredoxin or cytochrome is administered orally, topically, by inhalation, by injection, more specifically, intravenously, intramuscularly or subcutaneously.

In one embodiment, the methods may comprise co-administering to a patient one unit dose of compositions comprising a cupredoxin or cytochrome, or a variant, derivative or structural equivalent thereof, and one unit dose of compositions comprising an anti-malarial drug and/or an anti-HIV drug, in either order. These compositions may be administered at about the same time, or within about a given time following the administration of the other, for example, about one minute to about 60 minutes, or about 1 hour to about 12 hours of the other.

The invention also provides methods to inhibit the spread of the malaria parasite in an insect vector population harboring a malaria parasite by administering to an insect vector in the population at least one of a cupredoxin or cytochrome, or variant, derivative or structural equivalent of cupredoxin or cytochrome, at an amount that is effective to reduce the infectivity of the parasite in a co-existant mammalian population. In specific embodiments, the insect vector is a mosquito, and more specifically a mosquito from the species *Anopheles gambiae*. In this method, the administration of the cupredoxin or cytochrome, or variant, derivative or structural equivalent of cupredoxin or cytochrome can be accomplished by placing the peptides in compositions that will be consumed by the insect vector, however any manner that brings the peptide into contact with the malaria parasite in the insect vector's gut is contemplated. Many methods to administer chemicals to insect populations which produce such consumption are known in the art.

In another embodiment, a transmissible genetic element that passes from one mosquito to another will be operably connected to the cupredoxin coding sequence operably connected to a constitutive promoter, the cupredoxin or cytochrome, or variant, derivative or structural equivalent of cupredoxin or cytochrome will be produced inside the *Anopheles gambiae* infected with *P. falciparum* and will interfere with its replication/survival in the mosquito.

Other manners of administration of the peptides to the insect vector include, but are not limited to, fusing the cupredoxin or cytochrome, or variant, derivative or structural equivalent of cupredoxin or cytochrome genes to genes from other proteins normally consumed by the insects. The amount of peptides administered to the insect vector should be an amount effective to reduce the infectivity of the malaria parasite in a mammal when the insect vector comes into contact with a mammal. In specific embodiments, the amount administered should be effective to reduce the infectivity of the malaria parasite when the insect vector comes into contact with a human.

Mosquito larvae are suitable for use in the present invention and preferably, the promoter used is a strong promoter. Two alternative categories of promoter are available for use: inducible and constitutive promoters. Inducible promoters include, for example, heat shock promoters. Preferably, the heat shock promoter is an insect heat shock promoter, for example the *Drosophila melanogaster* hsp70 promoter, which is capable of driving the expression of genes in heterologous organisms, including medfly. The invention also encompasses the use of the medfly hsp70 promoter (Papadimitriou et al., Insect Mol Biol 7:279-90 (1998)). Alternative systems may be based on induction with the antibiotic tetracycline. (Heinrich and Scott, PNAS 97:8229-8232, (2000))

Heat shock promoters are inducible by raising the temperature of the conditions under which the medfly are being cultured. For example, at 23-25° C., the hsp70 promoter is active at low levels or not at all. This allows the insect larva to develop without stress induced by the production of a heterologous protein. At higher temperatures, however, such as 37-42° C., the hsp70 promoter is induced and expresses the heterologous protein at a high level.

Inducible promoters may be constructed based on known inducible gene control elements. For example, inducible promoters may be constructed by combining an element responsive to a drug or hormone which may be administered in the diet. In a preferred embodiment, a human oestrogen responsive element (ERE) may be used to regulate expression of the protein of interest, as long as the insect is transformed with a second coding sequence which expresses the human oestrogen receptor.

Constitutive promoters may also be used to express the protein and/or other proteins required in the insect larva. For example, the constitutive promoter may be a cytoplasmic actin promoter. The *D. melanogaster* cytoplasmic actin promoter has been cloned (Act5C) and is highly active in mosquitoes (Huynh and Zieler, J. Mol. Biol. 288:13-20 (1999)). Cytoplasmic actin genes and their promoters may also be isolated from other insects, including medfly. Other examples include the cytoplasmic tubulin promoter, for instance the medfly cytoplasmic tubulin promoter.

Promoters which control secreted polypeptides may be used, optionally together with appropriate signal sequences, to direct secretion of the protein to the haemolymph. For example, the larval serum protein promoter may be employed (Benes et al., Mol. Gen. Genet 249(5):545-556 (1995)).

Mass rearing technology for mosquitoes is highly developed. For protein production, larval cultures that have been initiated at different times can be synchronized by appropriate temperature shift regimes. This is possible because growth rates depend on the temperature of the environment; at 18° C. larval growth rates decrease by approximately 50%.

Pharmaceutical Compositions Comprising Cupredoxin and/or Cytochrome and Variants and Derivatives Thereof Pharmaceutical compositions comprising cupredoxin or cytochrome, or variant, derivative or structural equivalent thereof can be manufactured in any conventional manner, e.g., by conventional mixing, dissolving, granulating, dragee-making, emulsifying, encapsulating, entrapping, or lyophilizing processes. The substantially pure cupredoxin and/or cytochrome, and variants, derivatives and structural equivalents thereof can be readily combined with a pharmaceutically acceptable carrier well-known in the art. Such carriers enable the preparation to be formulated as a tablet, pill, dragee, capsule, liquid, gel, syrup, slurry, suspension, and the like. Suitable carriers or excipients can also include, for example, fillers and cellulose preparations. Other excipients can include, for example, flavoring agents, coloring agents, detackifiers, thickeners, and other acceptable additives, adjuvants, or binders. In some embodiments, the pharmaceutical preparation is substantially free of preservatives. In other embodiments, the pharmaceutical preparation may contain at least one preservative. General methodology on pharmaceutical dosage forms is found in Ansel et al., *Pharmaceutical Dosage Forms and Drug Delivery Systems* (Lippencott Williams & Wilkins, Baltimore Md. (1999)).

The composition comprising a cupredoxin or cytochrome, or variant, derivative or structural equivalent thereof used in the invention may be administered in a variety of ways, including by injection (e.g., intradermal, subcutaneous, intramuscular, intraperitoneal and the like), by inhalation, by topical administration, by suppository, by using a transdermal patch or by mouth. General information on drug delivery systems can be found in Ansel et al., Id. In some embodiments, the composition comprising a cupredoxin or cytochrome, or variant, derivative or structural equivalent thereof can be formulated and used directly as injectibles, for subcutaneous and intravenous injection, among others. The injectable formulation, in particular, can advantageously be used to treat patients that are at risk of an malaria-infection, likely to have an malaria-infection or have an malaria-infection. The composition comprising a cupredoxin or cytochrome, or variant, derivative or structural equivalent thereof can also be taken orally after mixing with protective agents such as polypropylene glycols or similar coating agents.

When administration is by injection, the cupredoxin or cytochrome, or variant, derivative or structural equivalent thereof may be formulated in aqueous solutions, specifically in physiologically compatible buffers such as Hanks solution, Ringer's solution, or physiological saline buffer. The solution may contain formulatory agents such as suspending, stabilizing and/or dispersing agents. Alternatively, the cupredoxin or cytochrome, or variant, derivative or structural equivalent thereof may be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide.

When administration is by intravenous fluids, the intravenous fluids for use administering the cupredoxin or cytochrome, or variant, derivative or structural equivalent thereof may be composed of crystalloids or colloids. Crystalloids as used herein are aqueous solutions of mineral salts or other water-soluble molecules. Colloids as used herein contain larger insoluble molecules, such as gelatin. Intravenous fluids may be sterile.

Crystalloid fluids that may be used for intravenous administration include but are not limited to, normal saline (a solution of sodium chloride at 0.9% concentration), Ringer's lactate or Ringer's solution, and a solution of 5% dextrose in water sometimes called D5W, as described in Table 2.

TABLE 2

Composition of Common Crystalloid Solutions

| Solution | Other Name | [Na$^+$] | [Cl$^-$] | [Glucose] |
|---|---|---|---|---|
| D5W | 5% Dextrose | 0 | 0 | 252 |
| ⅔ & ⅓ | 3.3% Dextrose/ 0.3% saline | 51 | 51 | 168 |
| Half-normal saline | 0.45% NaCl | 77 | 77 | 0 |
| Normal saline | 0.9% NaCl | 154 | 154 | 0 |
| Ringer's lactate* | Ringer's solution | 130 | 109 | 0 |

*Ringer's lactate also has 28 mmol/L lactate, 4 mmol/L K$^+$ and 3 mmol/L Ca$^{2+}$.

When administration is by inhalation, the cupredoxin or cytochrome, or variant, derivative or structural equivalent thereof may be delivered in the form of an aerosol spray from pressurized packs or a nebulizer with the use of a suitable propellant, e.g., dichlorodifluoromethane, trichlorofluoromethane, carbon dioxide or other suitable gas. In the case of a pressurized aerosol, the dosage unit may be determined by providing a valve to deliver a metered amount. Capsules and cartridges of, e.g., gelatin, for use in an inhaler or insufflator may be formulated containing a powder mix of the proteins and a suitable powder base such as lactose or starch.

When administration is by topical administration, the cupredoxin or cytochrome, or variant, derivative or structural equivalent thereof may be formulated as solutions, gels, ointments, creams, suspensions, and the like, as are well known in the art. In some embodiments, administration is by means of a transdermal patch. When administration is by suppository (e.g., rectal or vaginal), cupredoxin and/or cytochrome c and variants and derivatives thereof compositions may also be formulated in compositions containing conventional suppository bases.

When administration is oral, a cupredoxin or cytochrome, or variant, derivative or structural equivalent thereof can be readily formulated by combining the cupredoxin or cytochrome, or variant, derivative or structural equivalent thereof with pharmaceutically acceptable carriers well known in the art. A solid carrier, such as mannitol, lactose, magnesium stearate, and the like may be employed; such carriers enable the cupredoxin and/or cytochrome and variants and derivatives thereof to be formulated as tablets, pills, dragees, capsules, liquids, gels, syrups, slurries, suspensions and the like, for oral ingestion by a subject to be treated. For oral solid formulations such as, for example, powders, capsules and tablets, suitable excipients include fillers such as sugars, cellulose preparation, granulating agents, and binding agents.

Other convenient carriers, as well-known in the art, also include multivalent carriers, such as bacterial capsular polysaccharide, a dextran or a genetically engineered vector. In addition, sustained-release formulations that include a cupredoxin or cytochrome, or variant, derivative or structural equivalent thereof allow for the release of cupredoxin or cytochrome, or variant, derivative or structural equivalent thereof over extended periods of time, such that without the sustained release formulation, the cupredoxin or cytochrome, or variant, derivative or structural equivalent thereof would be cleared from a subject's system, and/or degraded by, for example, proteases and simple hydrolysis before eliciting or enhancing a therapeutic effect.

The half-life in the bloodstream of the compositions of the invention can be extended or optimized by several methods well known to those in the art, including but not limited to, circularized peptides (Monk et al., BioDrugs 19(4):261-78, (2005); DeFreest et al., J. Pept. Res. 63(5):409-19 (2004)), D,L-peptides (diastereomer), (Futaki et al., J. Biol. Chem. Feb 23; 276(8):5836-40 (2001); Papo et al., Cancer Res. 64(16):5779-86 (2004); Miller et al., Biochem. Pharmacol. 36(1):169-76, (1987)); peptides containing unusual amino acids (Lee et al., J. Pept. Res. 63(2):69-84 (2004)), N- and C-terminal modifications (Labrie et al., Clin. Invest. Med. 13(5):275-8, (1990)), and hydrocarbon stapling (Schafmeister et al., J. Am. Chem. Soc. 122:5891-5892 (2000); Walenski et al., Science 305:1466-1470 (2004)). Of particular interest are d-isomerization (substitution) and modification of peptide stability via D-substitution or L-amino acid substitution and hydrocarbon stapling.

In various embodiments, the pharmaceutical composition includes carriers and excipients (including but not limited to buffers, carbohydrates, mannitol, proteins, polypeptides or amino acids such as glycine, antioxidants, bacteriostats, chelating agents, suspending agents, thickening agents and/or preservatives), water, oils, saline solutions, aqueous dextrose and glycerol solutions, other pharmaceutically acceptable auxiliary substances as required to approximate physiological conditions, such as buffering agents, tonicity adjusting agents, wetting agents and the like. It will be recognized that, while any suitable carrier known to those of ordinary skill in the art may be employed to administer the compositions of this invention, the type of carrier will vary depending on the mode of administration. Compounds may also be encapsulated within liposomes using well-known technology. Biodegradable microspheres may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252.

The pharmaceutical compositions may be sterilized by conventional, well-known sterilization techniques, or may be sterile filtered. The resulting aqueous solutions may be packaged for use as is, or lyophilized, the lyophilized preparation being combined with a sterile solution prior to administration.

Administration of Cupredoxin and/or Cytochrome and Variants and Derivatives Thereof The cupredoxin or cytochrome, or variant, derivative or structural equivalent thereof can be administered formulated as pharmaceutical compositions and administered by any suitable route, for example, by oral, buccal, inhalation, sublingual, rectal, vaginal, transurethral, nasal, topical, percutaneous, i.e., transdermal or parenteral (including intravenous, intramuscular, subcutaneous and intracoronary) administration. The pharmaceutical formulations thereof can be administered in any amount effective to achieve its intended purpose. More specifically, the composition is administered in a therapeutically effective amount. In specific embodiments, the therapeutically effective amount is generally from about 0.01-20 mg/day/kg of body weight.

The compounds comprising cupredoxin or cytochrome, or variant, derivative or structural equivalent thereof are useful for the treatment and/or prophylaxis of malaria infection, alone or in combination with other active agents. The appropriate dosage will, of course, vary depending upon, for example, the compound of cupredoxin or cytochrome, or variant, derivative or structural equivalent thereof employed, the host, the mode of administration and the nature and severity of the conditions being treated. However, in general, satisfactory results in humans are indicated to be obtained at daily dosages from about 0.01-20 mg/kg of body weight. An indicated daily dosage in humans is in the range from about 0.7 mg to about 1400 mg of a compound of cupredoxin or cytochrome $c_{551}$, or variant, derivative or structural equivalent thereof conveniently administered, for example, in daily doses, weekly doses, monthly doses, and/or continuous dosing. Daily doses can be in discrete dosages from 1 to 12 times per day. Alternatively, doses can be administered every other day, every third day, every fourth day, every fifth day, every sixth day, every week, and similarly in day increments up to 31 days. Alternatively, dosing can be continuous using patches, i.v. administration and the like.

The method of introducing cupredoxin or cytochrome, or variant, derivative or structural equivalent thereof to patients is, in some embodiments, through the co-administration of cupredoxin or cytochrome, or variant, derivative or structural equivalent thereof with other drugs used for malaria therapy. Such methods are well-known in the art. In a specific embodiment, the cupredoxin and/or cytochrome c are part of an cocktail or co-dosing containing or with other malaria therapeutics. Malaria therapeutics of interest include, but are not limited to, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, proguanil, chloroquine, mefloquine, pyrimethamine-sulfadoxine, pyrimethamine-dapsone, halofantrine, quinine, proguanil, chloroquine, mefloquine, 1,16-hexadecamethylenebis(N-methylpyrrolidinium)dibromide, and combinations thereof.

The method of introducing cupredoxin or cytochrome $c_{551}$, or variant, derivative or structural equivalent thereof to patients is, in some embodiments, the same as currently used to introduce anti-HIV drugs, such as the protease-inhibitor-containing cocktails. Such methods are well-known in the art. In a specific embodiment, the cupredoxin or cytochrome $c_{551}$, or variant, derivative or structural equivalent thereof are part of an cocktail or co-dosing with anti-HIV therapeutics. Anti-HIV drugs include, but are not limited to, reverse transcriptase inhibitors: AZT (zidovudine [Retrovir]), ddC (zalcitabine [Hivid], dideoxyinosine), d4T (stavudine [Zerit]), and 3TC (lamivudine [Epivir]), nonnucleoside reverse transcriptase inhibitors (NNRTIS): delavirdine (Rescriptor) and nevirapine (Viramune), protease inhibitors: ritonavir (Norvir), a lopinavir and ritonavir combination (Kaletra), saquinavir (Invirase), indinavir sulphate (Crixivan), amprenavir (Agenerase), and nelfinavir (Viracept). In some embodiments, a combination of several drugs called highly active antiretroviral therapy (HAART) is used to treat the patients.

The exact formulation, route of administration, and dosage is determined by the attending physician in view of the patient's condition. Dosage amount and interval can be adjusted individually to provide plasma levels of the active cupredoxin or cytochrome, or variant, derivative or structural equivalent thereof which are sufficient to maintain therapeutic effect. Generally, the desired cupredoxin or cytochrome, or variant, derivative or structural equivalent thereof is administered in an admixture with a pharmaceutical carrier selected with regard to the intended route of administration and standard pharmaceutical practice.

In one aspect, the cupredoxin or cytochrome, or variant, derivative or structural equivalent thereof is delivered as DNA such that the polypeptide is generated in situ. In one embodiment, the DNA is "naked," as described, for example, in Ulmer et al., (Science 259:1745-1749 (1993)) and reviewed by Cohen (Science 259:1691-1692 (1993)). The uptake of naked DNA may be increased by coating the DNA onto a carrier, e.g., biodegradable beads, which are then efficiently transported into the cells. In such methods, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

Vectors, used to shuttle genetic material from organism to organism, can be divided into two general classes: cloning vectors are replicating plasmid or phage with regions that are essential for propagation in an appropriate host cell and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA, such as the DNA of a cupredoxin and/or a cytochrome. In expression vectors, the introduced DNA is operably-linked to elements such as promoters that signal to the host cell to highly transcribe the inserted DNA. Some promoters are exceptionally useful, such as inducible promoters that control gene transcription in response to specific factors. Operably-linking a cupredoxin or cytochrome and variants and derivatives thereof polynucleotide to an inducible promoter can control the expression of the cupredoxin or cytochrome and variants and derivatives thereof in response to specific factors. Examples of classic inducible promoters include those that are responsive to α-interferon, heat shock, heavy metal ions, and steroids such as glucocorticoids (Kaufman, *Methods Enzymol.* 185:487-511 (1990)) and tetracycline. Other desirable inducible promoters include those that are not endogenous to the cells in which the construct is being introduced, but, however, are responsive in those cells when the induction agent is exogenously supplied. In general, useful expression vectors are often plasmids. However, other forms of expression vectors, such as viral vectors (e.g., replication defective retroviruses, adenoviruses and adeno-associated viruses) are contemplated.

Vector choice is dictated by the organism or cells being used and the desired fate of the vector. In general, vectors comprise signal sequences, origins of replication, marker genes, polylinker sites, enhancer elements, promoters, and transcription termination sequences. As an example, one may clone a cupredoxin or a cytochrome gene into a vector transmissible in the malaria parasite-harboring mosquitoes to prevent the parasite from replicating inside the mosquitoes. The transmissibility of the vector will allow the spread of the cupredoxin/cytochrome to neighboring mosquitoes that are infected with the malaria parasites as well.

The exact formulation, route of administration, and dosage is determined by the attending physician in view of the patient's condition. Dosage amount and interval can be adjusted individually to provide plasma levels of the active cupredoxin and/or cytochrome and variants and derivatives thereof which are sufficient to treat the patient and/or maintain therapeutic effect. Generally, the desired cupredoxin and/or cytochrome and variants and derivatives thereof can be administered in an admixture with a pharmaceutical carrier selected with regard to the intended route of administration and standard pharmaceutical practice. Pharmaceutical compositions used in accordance with the present invention can be formulated in a conventional manner using one or more physiologically acceptable carriers comprising excipients and auxiliaries that facilitate processing of the cupredoxin and/or cytochrome and variants and derivatives thereof, active agents, for inhibiting or stimulating the secretion of cupredoxin and/or cytochrome and variants and derivatives thereof, or a mixture thereof into preparations which can be used therapeutically.

Kits Comprising Cupredoxin and/or Cytochrome C and Variants and Derivatives Thereof In one aspect, the invention provides kits containing one or more of the following in a package or container: (1) a biologically active composition comprising a cupredoxin or cytochrome, or variant, derivative or structural equivalent thereof; (2) a pharmaceutically acceptable adjuvant or excipient; (3) a vehicle for administration, such as a syringe; (4) instructions for administration. Embodiments in which two or more of components (1)-(4) are found in the same container are also contemplated.

In another aspect, the invention provides kits containing one or more of the following in a package or container: (1) a biologically active composition comprising a cupredoxin or cytochrome, or variant, derivative or structural equivalent thereof; (2) an malaria therapeutic, including, but not limited to, proguanil, chlorproguanil, trimethoprim, chloroquine, mefloquine, lumefantrine, atovaquone, pyrimethamine-sulfadoxine, pyrimethamine-dapsone, halofantrine, quinine, quinidine, amodiaquine, amopyroquine, sulphonamides, artemisinin, arteflene, artemether, artesunate, primaquine, pyronaridine, proguanil, chloroquine, mefloquine, pyrimethamine-sulfadoxine, pyrimethamine-dapsone, halofantrine, quinine, proguanil, chloroquine, mefloquine, 1,16-hexadecamethylenebis(N-methylpyrrolidinium)dibromide; (3) a pharmaceutically acceptable adjuvant or excipient; (4) a vehicle for administration, such as a syringe; (5) instructions for administration. Embodiments in which two or more of components (1)-(5) are found in the same packaging or container are also contemplated.

In some embodiments, the kit also comprises an anti-HIV therapeutic in a package or container. Anti-HIV therapeutics of interest include, but are not limited to, reverse transcriptase inhibitors: AZT (zidovudine [Retrovir]), ddC (zalcitabine [Hivid], dideoxyinosine), d4T (stavudine [Zerit]), and 3TC (lamivudine [Epivir]), nonnucleoside reverse transcriptase inhibitors (NNRTIS): delavirdine (Rescriptor) and nevirapine (Viramune), protease inhibitors: ritonavir (Norvir), a lopinavir and ritonavir combination (Kaletra), saquinavir (Invirase), indinavir sulphate (Crixivan), amprenavir (Agenerase), and nelfinavir (Viracept). In some embodiment, a combination of several drugs called highly active antiretroviral therapy (HAART) is included in the kit.

When a kit is supplied, the different components of the composition may be packaged in separate containers and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain the lyophilized polypeptide or polynucleotide of cupredoxin and/or cytochrome c and variants and derivatives thereof, or buffers that have been packaged under a neutral, non-reacting gas, such as nitrogen. Ampules may consist of any suitable material, such as glass, organic polymers, such as polycarbonate, polystyrene, etc., ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device, etc. Detailed instructions may not be physically associated with the kit; instead, a user may be directed to an internet web site specified by the manufacturer or distributor of the kit, or supplied as electronic mail.

Modification of Cupredoxin and/or Cytochrome

Cupredoxin or cytochrome may be chemically modified or genetically altered to produce variants and derivatives as explained above. Such variants and derivatives may be synthesized by standard techniques.

In addition to naturally-occurring allelic variants of cupredoxin and cytochrome, changes can be introduced by mutation into cupredoxin or cytochrome coding sequence that incur alterations in the amino acid sequences of the encoded cupredoxin or cytochrome that do not significantly alter the ability of cupredoxin or cytochrome to inhibit parasitemia in malaria-infected red blood cells. A "non-essential" amino acid residue is a residue that can be altered from the wild-type sequences of the cupredoxin without altering biological activity, whereas an "essential" amino acid residue is required for such biological activity. For example, amino acid residues that are conserved among the cupredoxins are predicted to be particularly non-amenable to alteration, and thus "essential."

Amino acids for which conservative substitutions that do not change the activity of the polypeptide can be made are well known in the art. Useful conservative substitutions are shown in Table 3, "Preferred substitutions." Conservative substitutions whereby an amino acid of one class is replaced with another amino acid of the same type fall within the scope of the invention so long as the substitution does not materially alter the biological activity of the compound.

TABLE 3

Preferred substitutions

| Original residue | Exemplary substitutions | Preferred substitutions |
| --- | --- | --- |
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Non-conservative substitutions that affect (1) the structure of the polypeptide backbone, such as a β-sheet or α-helical conformation, (2) the charge, (3) hydrophobicity, or (4) the bulk of the side chain of the target site can modify the cytotoxic factor function. Residues are divided into groups based on common side-chain properties as denoted in Table 4. Non-conservative substitutions entail exchanging a member of one of these classes for another class. Substitutions may be introduced into conservative substitution sites or more specifically into non-conserved sites.

TABLE 4

Amino acid classes

| Class | Amino acids |
| --- | --- |
| hydrophobic | Norleucine, Met, Ala, Val, Leu, Ile |
| neutral hydrophilic | Cys, Ser, Thr |

TABLE 4-continued

Amino acid classes

| Class | Amino acids |
| --- | --- |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis (Carter, Biochem J. 237:1-7 (1986); Zoller and Smith, Methods Enzymol. 154:329-350 (1987)), cassette mutagenesis, restriction selection mutagenesis (Wells et al., Gene 34:315-323 (1985)) or other known techniques can be performed on the cloned DNA to produce the cupredoxin or cytochrome C551 variant DNA.

Known mutations of cupredoxins and cytochrome $c_{551}$ can also be used to create variant cupredoxin and cytochrome $c_{551}$ to be used in the methods of the invention. For example, the C112D and M44KM64E mutants of azurin are known to have cytotoxic and growth arresting activity that is different from the native azurin, and such altered activity can be useful in the treatment methods of the present invention. One embodiment of the methods of the invention utilize cupredoxin and/or cytochrome and variants and derivatives thereof retaining the ability inhibit the growth of malaria infection in mammalian cells. In another embodiment, the methods of the present invention utilize cupredoxin variants such as the M44KM64E mutant, having the ability to cause cellular growth arrest.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended embodiments.

EXAMPLES

Example 1

In Vitro Inhibition of *P. falciparum* Parasitemia by Cupredoxin and Cytochrome

The cupredoxins bacterial wt azurin, M44KM64E azurin, rusticyanin and cyanobacterial plastocyanin, as well as the cytochromes *Pseudomonas aeruginosa* cytochrome $c_{551}$, human cytochrome c and *Phormidium laminosum* cytochrome f were tested in a normal red blood cell (RBC) assay at 200 µg/ml concentrations at 30 hours post inoculation. In these experiments, the normal RBCs were washed twice in serum free media and resuspended to 10% hematocrit in complete RPMI. 200 µl of 10% Hct RBCs were added to each of 24 wells (final 2% Hct at 1 ml) in addition to 30 µl complete RPMI containing recombinant cupredoxin or cytochrome proteins at 666 µM for a final concentration of 200

μM. Schizont-stage parasites were prepared by centrifuging a late-stage culture through a Percoll cushion at 3200 rpm for 10 minutes. For infection, 4×10⁶ parasites/well in 500 μl volume were added at t=0 hr. The plate was incubated for 30 hours and scored by thin blood smear and Giemsa stain at that time.

The control showed 9.5% parasitemia (standard error 1.3%), wt azurin 6.9% (s.e. 1.4%), M44KM64E azurin 9.1% (s.e. 1.0%), rusticyanin 7.2% (s.e. 0.7%), cytochrome $c_{551}$ 7.5% (s.e. 1.5%), human cytochrome c 8.4% (s.e. 0.4%), plastocyanin 8.1% (s.c. 1.3%) and cytochrome f 6.6% (s.e. 1.0%), suggesting that cupredoxins such as wt azurin and rusticyanin and cytochromes such as cytochrome f or cytochrome $c_{551}$ demonstrated 20 to 30% inhibition of parasitemia.

When the cupredoxins were tested for their effects at various stages of the parasite life cycle (0-24 hours, ring formation; 24-36 hours, trophozoite; 36-48 hours, schizont), the control showed 0.1% average ring formation and 9.4% trophozoite formation while wt azurin showed no ring formation but 6.9% trophozoite formation; cytochrome f showed 0.2% ring formation but had significantly low (6.3%) trophozoite formation. Remarkably, rusticyanin exhibited very high (2.0%) ring formation and significantly reduced (5.2%) trophozoite formation. The others had no significant effect. The parasites in rusticyanin-treated samples looked sick and dying as compared to the rest of the samples, showing a significant inhibitory and toxic effect of rusticyanin on parasite development.

Example 2

Inhibition In Vitro of *P. falciparum* Intracellular Replication by Rusticyanin

To determine if the bacterial redox proteins can inhibit intracellular replication of the malarial parasites, red blood cells were loaded to an intracellular recombinant protein concentration of 200 μg/ml using a hypotonic ghost preparation. Cells where then washed, resuspended and infected with schizont-stage parasites (*P. falciparum*) as described in Example 1. The red blood cell ghosts were incubated for 19 hours and 40 hours and giemsa smears were made.

Compared to the infections of normal red blood cells in Example 1, only rusticyanin decreased total parasitemia in loaded cell ghost cultures. At 19 hours, there was no significant difference in invasion and ring formation, with empty ghosts at 5.0±0.4% and rusticyanin-loaded ghosts at 4.5±1.0%. However, at 40 hours, rusticyanin-loaded ghosts had a lower level of infection. No major effects were seen at 19 hour with any of the bacterial proteins. However, at 40 hours, control untreated ghosts showed 4.6±0.3% parasitemia while rusticyanin-treated ghosts had 2.7±0.8% parasitemia, an almost 50% reduction. See, Table 5. Wt azurin, M44KM64E mutant azurin, plastocyanin, cytochrome $c_{551}$, human cytochrome c and cynobacterial cytochrome f proteins showed parasitemia varying from 4.2 to 5.4%.

TABLE 5

Cupredoxin and cytochrome inhibition of *P. falciparum* infection of red blood cell ghosts.

| Treatment | Mean Parasitemia at 40 hr | Std. Error |
|---|---|---|
| Empty | 4.6% | 0.3% |
| Wild Type Azurin | 5.4% | 1.0% |
| M44KM64E Azurin | 4.7% | 0.5% |
| Rusticyanin | 2.7% | 0.8% |
| Cytochrome $c_{551}$ | 4.2% | 0.4% |
| Human Cytochrome c | 4.6% | 0.8% |
| Plastocyanin | 4.3% | 0.3% |
| Cytochrome f | 4.5% | 0.9% |

Example 3

Structural Homology Between Azurin and Fab Fragment of G17.12 Monoclonal Antibody Complexed with Pf MSP1-19

Previous studies have shown that cupredoxins show structural similarity to the variable domains of the immunoglobulin superfamily members. (Gough & Chothia, Structure 12:917-925 (2004); Stevens et al., J. Mol. Recognit. 18:150-157 (2005)) The DALI algorithm (Holm & Park, Bioinformatics 16:566-567 (2000)) was used to search the 3D databases for structural homologs of azurin (1JZG) from *P. aeruginosa*. Azurin exhibits structural similarity to the Fab fragment of G17.12 monoclonal antibody in complexation with Pf MSP1-19 fragment of the MSP1 merozoite surface protein of *P. falciparum*. (Pizarro et al., J. Mol. Biol. 328:1091-1103 (2003).) (Table 6) Azurin also exhibits a structural similarity to ICAM-1 (Table 6), which is involved in cerebral malaria and implicated as a receptor on the endothelial cells in the microvasculature of the brain and other tissues for sequestering *P. falciparum*-infected erythrocytes. (Smith et al., Proc. Natl. Acad. Sci. USA 97:1766-1771 (2000); Franke-Fayard et al., Proc. Natl. Acad. Sci. USA 102:11468-11473 (2005))

This example shows that cupredoxins including azurin demonstrate structural similarities in having two anti-parallel β sheets packed face to face and linked by a disulfide bridge to the variable domains of the immunoglobulin superfamily members as well as extracellular domains of the intercellular adhesion molecules (ICAM) and their ligands.

TABLE 6

Structural similarity of *P. aeruginosa* azurin with various pathogenesis-related proteins

| PDB | Annotation | Reference | Azurin (1jzg) DALI z score[1] |
|---|---|---|---|
| 1VCAB1 | Human Vascular Cell Adhesion Molecle-1, VCAM-1 | 17 | 3.5 |
| 1ZXQ1 | The Crystal Structure of ICAM-2 | 19 | 3.3 |
| 1IAM1 | Structure of The Two Amino-Terminal Domains of, ICAM-1 | 20 | 3.0 |
| 1OB1 A1 | Crystal Structure of a Fab complex with *Plasmodium falciparum* MSP1-19 | 21 | 2.9 |
| 1TOP B | The complex Structure of Binding Domains of ICAM-3 and Alphabeta2 | 22 | 2.5 |
| 2NCM | Neural Cell Adhesion Molecule, NCAM | 23 | 2.4 |

[1] Structural alignment to azurin were made using DALI (16). Structure pairs with DALI z scores <2 are considered dissimilar.

Example 4

Cloning and Expression of the Laz and H.8-Azurin Fusion Genes

The laz gene from *Neisseria gonorrhoeae* was cloned based on its known sequence (SEQ ID NO: 22). The *P. aeruginosa* azurin gene (SEQ ID NO: 1), termed paz, and the sequence of the H.8 epitope of laz from *N. gonnerrhoeae* (SEQ ID NO: 21), were used to clone in frame the H.8 epitope gene in the 5'-end of paz to produce H.8-paz or in the 3'-end of paz to generate paz-H.8.

TABLE 7

Cancer cells, bacterial strains and genetic constructs

| Cells/strains/ plasmids | Relevant characteristics* | Reference |
|---|---|---|
| *P. aeruginosa* PAO1 | Prototroph, FP- (sex factor minus) | Holloway, et al., Microbiol. Rev. 43: 73-102 (1979) |
| *E. coli* JM109 | Cloning and azurin expression strain | Yanisch-Perron, et al., Gene 33: 103-119 (1985) |
| *E. coli* BL21 (DE3) | GST expression strain | Novagen |
| *N. gonorrhoeae* F62 | Prototroph used for DNA isolation | American Type Culture Collection |
| pUC18 | General cloning vector, Ap$^r$ | Yanisch-Perron, et al., id. |
| pUC19 | General cloning vector, Ap$^r$ | Yanisch-Perron, et al., id. |
| pUC18-laz | A 1 kb PCR fragment from genomic DNA of *N. gonorrhoeae* F62 cloned into pUC18 | Herein |
| pUC19-paz | A 0.55 kb PCR fragment from *P. aeruginosa* PAO1 cloned into HindIII and PstI digested pUC19, Ap$^r$ | Yamada, et al., Proc. Natl. Acad. Sci. USA 99: 14098-14103 (2002); Yamada, et al., Proc. Natl. Acad. Sci. USA 101: 4770-4775 (2004) |
| pUC18-H.8-paz | Fusion plasmid encoding H.8 from *N. gonorrhoeae* and azurin from *P. aeruginosa* PAO1, Ap$^r$ | Herein |
| pGEX-5X-3 | GST gene fusion vectors, Ap$^r$ | Amersham |
| pET29a | *E. coli* expression vector, Km$^r$ | Novagen |
| pET29a-gst | pET29a derivative containing the gst gene, Km$^r$ | Herein |
| pGEX-5X-3-H.8 | pGEX-5X-3 derivative containing H.8-encoding region, Ap$^r$ | Herein |
| pET29a-gst-H.8 | pET29a derivative containing gst-H.8 gene, Km$^r$ | Herein |

*Ap, ampicillin; Km, kanamycin; GST, Glutathione S-transferase.

Cloning and Expression of the Paz and Laz Genes.

The cloning and hyperexpression of the azurin gene has been described. (Yamada, et al., Proc. Natl. Acad. Sci. USA 99:14098-14103 (2002); Punj, et al., Oncogene 23:2367-2378 (2004)) The Laz-encoding gene (laz) of *Neisseria gonorrhoeae* was amplified by PCR with genomic DNA of *N. gonorrhoeae* strain F62 as template DNA. The forward and reverse primers used were 5'-CCG GAATTCCGGCAGGGATGTTGTAAATATCCG-3' (SEQ ID NO: 23) and 5'-GG GGTACCGCCGTGGCAGGCATACAGCATTTCAATCGG-3' (SEQ ID NO: 24) where the additionally introduced restriction sites of EcoRI and KpnI sites are underlined respectively. The amplified DNA fragment of 1.0 kb, digested with EcoRI and KpnI, was inserted into the corresponding sites of pUC18 vector (Yanisch-Perron, et al., Gene 33:103-119 (1985)) so that the laz gene was placed downstream of the lac promoter to yield an expression plasmid pUC18-laz (Table 7).

The plasmids expressing fusion H.8 of *N. gonorrhoeae* Laz and azurin of *P. aeruginosa* (Paz) were constructed by PCR with pUC19-paz and pUC18-laz as templates. For H.8-Paz fusion, a 3.1 kb fragment was amplified with pUC18-laz as a template and primers, 5'-(phosphorylated) GGCAGCAGGGGCTTCGGCAGCATCTGC-3' (SEQ ID NO: 25) and 5'-CTGCAG GTCGACTCTAGAGGATCCCG-3' (SEQ ID NO: 26) where a SalI site is underlined. A PCR amplified a 0.4 kb fragment was obtained from pUC19-paz as a template and primers, 5'-(phosphorylated)GCCGAGTGCTCGGTGGA-CATCCAGG-3' (SEQ ID NO: 27) and 5'-TA CTCGAGTCACTTCAGGGTCAGGGTG-3' (SEQ ID NO: 28) where a XhoI site is underlined. A SalI digested PCR fragment from pUC18-laz and XhoI digested PCR fragment from pUC19-paz were cloned to yield an expression plasmid pUC18-H.8-paz (Table 7).

*E. coli* JM109 was used as a host strain for expression of azurin and its derivative genes. Recombinant *E. coli* strains were cultivated in 2×YT medium containing 100 μg/ml ampicillin, 0.1 mM IPTG and 0.5 mM CuSO$_4$ for 16 h at 37° C. to produce the azurin proteins.

When *E. coli* strains harboring these plasmids were grown in presence of IPTG, cells lysed and the proteins purified as described for azurin (Yamada, et al., Proc. Natl. Acad. Sci. USA 99:14098-14103 (2002); Punj, et al., Oncogene 23:2367-2378 (2004); Yamada, et al., Cell. Microbiol. 7:1418-1431 (2005)), the various azurin derivatives migrated on SDS-PAGE as single components, although the H.8 containing proteins (about 17 kDa) showed anomalous migrations, as noted before (Cannon, Clin. Microbiol. Rev. 2:S1-S4 (1989); Fisette, et al., J. Biol. Chem. 278:46252-46260 (2003)).

Plasmid Construction for Fusion GST Proteins.

Plasmids expressing fusion glutathione S-transferase (GST)-truncated wt-azurin (azu) derivatives were constructed by a polymerase chain reaction using proofreading DNA polymerase. For pGST-azu 36-128, an amplified PCR fragment was introduced into the BamHI and EcoRI sites of the commercial GST expression vector pGEX-5X (Amersham Biosciences, Piscataway, N.J.). The fragment was amplified with pUC 19-azu as a template and primers, 5'-C GGGATCCCCG GCA ACC TGC CGA AGA ACG TCA TGG GC-3' (SEQ ID NO: 29) and 5'-CGGAATTC GCA TCA CTT CAG GGT CAG GG-3' (SEQ ID NO: 30), where the additionally introduced BamHI and EcoRI sites are underlined respectively. Carboxyl-terminus truncation of azu gene was cumulatively performed by introducing a stop codon using QuickChange site-direct mutagenesis kit (Stratagene, La Jolla, Calif.).

For pGST-azu 36-89, a stop codon were introduced into Gly90. The plasmid carrying pGST-azu 36-128 was used as template DNA. Three sets of oligonuclotides for site-direct mutagenesis are shown as follows. For pGST-azu 36-89: 5'-CCA AGC TGA TCG GCT CGT GAG AGAAGG ACT CGG TGA CC-3' (SEQ ID NO: 31), and 5'-GGT CAC CGA GTC CTT CTC TCA CGA GCC GAT CAG CTT GG-3 (SEQ ID NO: 32).

For pGST-azu 88-113, carboxyl terminus truncation of azu gene was cumulatively performed by introducing stop codon using QuickChange site directed mutagenesis kit (Stratagene, La Jolla, Calif.). For pGST-azu 88-113, a stop codon was introduced into Phe114. The plasmid carrying pGST-azu 88-128 was used as the template. For pGST-azu 88-128 an amplified PCR fragment was introduced into the BamHl and EcoR1 sites of the commercial GST expression vector pGEX-5X (Amersham Biosciences). The fragment was amplified with pUC 19-azu as the template and primers, 5'-CGGGGATCC CCG GCT CGG GCG AGA AGG AC-3' (SEQ ID NO: 33) and 5'-CGGGAATTC TCC ACT TCA GGG TCA GGG TG-3' (SEQ ID NO: 34) where the additionally introduced BamHl and EcoR1 sites are underlined respectively.

One set of oligonucleotides for site directed mutagenesis are shown as follows for the preparation of pGST-azu 88-113: 5'-GTT CTT CTG CAC CTA GCC GGG CCA CTC CG-3' (SEQ ID NO: 35) and 5'-CGG AGT GGC CCG GCT AGG TGC AGA AGA AC-3' (SEQ ID NO: 36). pGST-azu 88-113 was used to transform E. coli XL-1 Blue strains. Plasmid extraction was performed using a commercial kit (Qiagen, Venlo, The Netherlands) and PCR sequencing were performed to assess plasmid insertion and transfection.

E. coli BL21 (DE3) was used as a host strain for expression of the gst and its fusions derivatives. E. coli strain XL1-Blue transformed with pGST-azu plasmids was grown in LB media with ampicillin for three hours at 37° C. upon which IPTG induction (0.4 mM) was performed an subsequent incubation for 2-4 h at 37° C. to maximize the expression levels. Cells were isolated by centrifugation, resuspended in 25 mL of 1×PBS buffer. Subsequent cell lysis involved two sequential treatments of the cell suspension via sonication (20 min on ice) and heat-cold shock in acetone-dry ice bath (using the appropriate protease inhibitors). Supernatants of the cell lysis mixture were isolated and passed through a freshly packed and PBS equilibrated 1 mL glutathione-sepharose 4B (Amersham Biosciences) column. After column washing and subsequent elution of GST-azu product using 10 mM glutathione in 20 mM Tris-HCl pH 8. GST-Azu 88-113 purity was tested via electrophoresis using a 10% SDS-PAGE Tris-Gly gel stained with Coomassie Brilliant Blue R reagent. Protein concentration was determined using the Bradford Method.

Example 5

Azurin Binds to the C-Terminal Fragments MSP1-19 and MSP1-42 of the *P. falciparum* Merozoite Surface Protein MSP1

Given the structural similarity (Table 6) between azurin and the fab fragment of the monoclonal antibody G17.12 in complexation with Pf MSP1-19 (Pizarro et al., id), the ability of azurin to form a complex with Pf MSP1-42 or Pf MSP1-19 was determined. Two derivatives of azurin, Laz, an azurin-like protein from gonnococci and meningococci such as *Neisseria meningitidis* with an additional 39 amino acid epitope called an H.8 epitope (Gotschlich & Seiff, FEMS Microbiol. Lett. 43:253-255 (1987); Kawula et al., Mol. Microbiol. 1:179-185 (1987)) and H.8-azurin, where the H.8 epitope of Laz has been fused in the N-terminal part of *P. aeruginosa* azurin in frame (as described in Example 4) were tested.

In vitro protein-protein interactions were evaluated using a Biacore X spectrometer from Biacore AB International. All experiments were conducted at 25° C. in HBS-EP running buffer (0.01 M HEPES, pH 7.4, 0.15 M NaCl, 3 mM EDTA, 0.005% v/v Surfactant P20) using Au-CM5 sensor chips (Biacore). Protein immobilizations on CM5 chips were conducted according to the amine coupling procedure. Proteins were immobilized after NHS/EDC preactivation of the CM5 surface: 50 μl injections of azurin (510 μM). Subsequent treatment of CM5 surface with ethanolamine (1M, pH 8.8) removed uncrosslinked proteins. Binding studies were performed by injecting protein eluents (50 μl) over the protein-CM5 surface at flow rates of 30 μl/min with a 120 sec time delay at the end of the injections. Protein eluents included GST-azurin fusion proteins (GST, GST-Azu 36-128, GST-Azu 36-89, and GST-Azu 88-113, as described in Example 4). Sensor chip surfaces were regenerated between protein injections using 100 mM NaOH (10 μl injection pulse). All binding studies were run in parallel against a negative flow channel with bare Au-CM5 sensor surface to correct for nonspecific binding to the chips. To generate binding constant data, titration experiments were designed via injection of increasing concentrations of protein eluents (0.05-2000 nM). The SPR data were fit to a Langmuir (1:1) equilibrium binding model [Req=Rmax/(1+Kd/C] as specified in the Biacore software from which binding constants (Kd) were extrapolated.

Specific interactions of the Pf MSP1-19 and Pf MSP1-42 proteins with azurin, H.8-azurin and Laz were determined by surface plasmon resonance (SPR) analysis and the data are presented in FIG. 1. SPR sensorgrams for binding of immobilized Pf MSP1-19 and Pf MSP1-42 with azurin and its derivatives indicated selective recognition among these proteins. While nanomolar concentrations of azurin allowed significant binding with the immobilized MSP1-19 (FIG. 1A) or MSP1-42 (FIG. 1B), both H.8-azurin and Laz demonstrated a higher affinity of binding with the merozoite surface protein MSP1 cleavage products, with characteristic Kd values of 32.2 nM between azurin and MSP1-19 and 54.3 nM between azurin and MSP1-42. The Kd values between H.8-azurin and MSP1-19 and MSP1-42 were 11.8 nM and 14.3 nM while such values between Laz and MSP1-19 and MSP1-42 ranged from 26.2 nM and 45.6 nM respectively.

To examine if the H.8 epitope might facilitate binding of the H.8-azurin or Laz to the PfMSP1-19 or PfMSP1-42 moieties, the ability of glutathione S-transferase (GST) and a fusion derivative H.8-GST where the H.8 epitope was fused in the N-terminal of GST (see Example 4), to bind MSP1-19 or MSP1-42 was tested. Neither the GST nor the H.8-GST bound PfMSP1-19 (FIG. 1A) or MSP1-42 (FIG. 1B), although H.8-GST showed a weak binding with MSP1-42.

Glutathione S transferase (GST) and some of the fusion proteins where parts of azurin were fused to GST (Yamada et al., Cell. Microbiol. 7:1418-1431 (2005), and Example 4) were tested for their ability to bind to MSP1-19. GST alone, or GST-Azu 88-113, where the azurin amino acid sequence 88 to 113 out of 128 amino acids of azurin was fused to GST in frame, did not show any binding (FIG. 1C) while GST-Azu 36-89 with amino acid sequence 36 to 89 and GST-Azu 36-128 with amino acid sequence 36 to 128 showed significant binding with MSP1-19 with Kd values of 20.9 nM and 24.5 nM respectively.

Example 6

Inhibition of *Plasmodium falciparum* Parasitemia by Azurin, H.8-Azurin and Laz

The extent of parasitemia was determined using schizont stage parasites and normal red blood cells (RBC). Normal red blood cells (RBCs) were washed twice in serum-free medium and resuspended to 10% hematocrit in complete RPMI. 200 μl of 10% hematocrit RBCs were added to each of 24 wells in addition to 300 μl complete RPMI without or with azurin, H.8-azurin or Laz at various concentrations. Schizont stage *P. falciparum* parasites were prepared by centrifuging a late-stage culture through a Percoll cushion at 3200 rpm for 10 min. For infection, $4 \times 10^6$ parasites per well in 500 μl volume were added at time zero. The plate was incubated overnight (about 16 h) and then scored by thin blood smear and Giemsa stain at that time.

Azurin, H.8-azurin or Laz all demonstrated significant inhibition of parasitemia in a dose-dependent manner (FIG. 2), although at relatively high concentrations (about 50 μM). Such high concentrations presumably reflect the multiple ways the malarial parasites invade the erythrocytes (Cowman et al., FEBS Lett. 476:84-88 (2000); Baum et al., J. Biol. Chem. 281:5197-5208 (2006)) and a high concentration of azurin or Laz is necessary to interfere in the entry process. As indicated by their enhanced binding affinities to MSP1-19, both H.8-azurin and Neisserial Laz protein showed a higher level of inhibition of *P. falciparum* parasitemia as compared to azurin (FIG. 2).

When azurin was labeled with the red fluorescent dye Alexa fluor 568 and used during the invasion assay, very little red fluorescence was detectable inside the RBC, suggesting that azurin seems not to enter the RBC as part of bound MSP1-19, or more likely, that the RBCs that showed the presence of the schizonts were the ones where azurin failed to bind with the MSP1-19. These data fully agree with our previous observation (Yamada et al., Cell. Microbiol. 7:1418-1431 (2005)) that azurin does not enter normal cells such as macrophages, mast cells, etc, and the effect of azurin, H.8-azurin or Laz is at the entry level rather than the intracellular replication of the parasite. Taken together, the data in FIG. 2 demonstrate the potential antimalarial action of azurin, H.8-azurin and Laz through interference in the invasion of the RBC by the parasites.

Example 7

Azurin Binds ICAMs

An interesting structural similarity between azurin and ICAMs (Table 6) that are known to be involved as receptors for *P. falciparum*-infected erythrocytes (Wassmer et al., PloS Med. 2:885-890 (2005); Dormeyer et al., Antimicrob. Agents Chemotherap. 50:724-730 (2006)) prompted test analysis of protein-protein interactions as measured by SPR between azurin and ICAMs such as ICAM-1, ICAM-2, ICAM-3 and NCAM. With immobilized azurin on the CM5 chip, ICAM-3 (FIG. 3, Kd=19.5±5.4 nM) and NCAM (FIG. 3, inset), but interestingly not ICAM-1 and ICAM-2, showed strong binding. While not limiting the manner in which the invention operates, part of effect of azurin on inhibition of *P. falciparum* parasitemia might also be mediated through its interaction with ICAM-3 or NCAM.

Example 8

Treatment of Patients Likely Exposed to or Exposed to Malaria

Clinical use for the prevention malaria, a pharmaceutical comprising one or more cupredoxin and/or a cytochrome is administered to a patient.

Fifteen healthy male volunteers, aged 22-50, who have a no history of preexisting antibodies to blood-stage *P. falciparum* parasites, as determined by immunofluorescent assay, but reside in an area where malaria is endemic, will be injected with a pharmaceutical preparation of purified cupredoxin and purified cytochrome. Two such men will serve as non-treated controls.

The sterile pharmaceutical preparation is in the form of 0.5 ml single-dose ampules of sterile *Pseudomonas aeruginosa* azurin in a pharmaceutical preparation designed for intraveneous administration, as will be well known to those in the art. The pharmaceutical preparation is stored at 4° C. and protected from light before administration. In one clinical trial, azurin is prepared at five different concentrations: 10 μg, 30 μg, 100 μg, 300 μg and 800 μg azurin per 0.5 ml dose.

The pharmaceutical preparation is given intraveneously to thirteen volunteers for each 10 doses. Volunteers receive primary treatment at day 0 and subsequent doses identical doses at every other day for three weeks. Volunteers are observed for immediate toxic effects for twenty minutes after injection. Twenty-four and forty-eight hours later, they are examined for evidence of fever, local tenderness, erythema, warmth, induration and lymphadenopathy, and are asked about complaints of headache, fever, chills, malaise, local pain, nausea and joint pain. Before each dose, blood and urine samples are taken for full laboratory examination. Complete blood count and serum chemistry profiles are rechecked two days after each dose. The presence of the malaria parasite are determined by light microscopic examination (ME) of the stained blood smears, or the ICT Malaria P.f./P.v. test kits (Binax, Inc., Portland, Me.). The results demonstrate the effectiveness of the therapy.

Example 9

Control of Malaria Infection of Insects

A transmissible genetic element that passes from one mosquito to another will be operably connected to the cupredoxin coding sequence operably connected to a constitutive promoter. The *P. aeruginosa* azurin will therefore be produced inside the *Anopheles gambiae* infected with *P. falciparum* and will interfere with its replication/survival in the mosquito. This mosquito will then be introduced to an endemic area so that the azurin-harboring genetic element will spread to other *P. falciparum*-infected *A. gambiae* mosquitoes, inhibiting *P. falciparum* growth or survival.

Example 10

Treatment of Patients Infected by Malaria

Clinical use of a malaria therapy, comprising one or more cupredoxin and/or a cytochrome, for treatment of malaria infection in humans.

Fifteen healthy male volunteers, aged 22-50, who exhibit a history of preexisting antibodies to blood-stage *P. falciparum* parasites, as determined by immunofluorescent assay, are injected with a pharmaceutical preparation of purified *P. aeruginosa* azurin. Two such men serve as treated controls.

The sterile pharmaceutical preparation is in the form of 0.5 ml single-dose ampules of sterile *P. aeruginosa* azurin in a pharmaceutical preparation designed for intraveneous administration, as will be well known to those in the art. The pharmaceutical preparation is stored at 4° C. and protected from light before administration. In one clinical trial, *P. aeruginosa* azurin is prepared at five different concentrations: 10 μg, 30 μg, 100 μg, 300 μg and 800 μg azurin/cytochrome $c_{551}$ (1:1 on molecule basis) per 0.5 ml dose.

The pharmaceutical preparation is given intraveneously to thirteen volunteers for each 10 doses. Volunteers receive primary treatment at day 0 and subsequent doses identical doses at every other day for three weeks. Volunteers are observed for immediate toxic effects for twenty minutes after injection. Twenty-four and forty-eight hours later, they are examined for evidence of fever, local tenderness, erythema, warmth, induration and lymphadenopathy, and are asked about complaints of headache, fever, chills, malaise, local pain, nausea and joint pain. Before each dose, blood and urine samples are taken for full laboratory examination. Complete blood count and serum chemistry profiles are rechecked two days after each dose. The presence of the malaria parasite are determined by light microscopic examination (ME) of the stained blood smears, or the ICT Malaria P.f./P.v. test kits (Binax, Inc., Portland, Me.). The results demonstrate the effectiveness of the therapy.

What is claimed:

1. An isolated peptide consisting of residues 36-89 of SEQ ID NO. 1 that can inhibit parasitemia in malaria-infected red blood cells.

2. The isolated peptide of claim 1 which can inhibit parasitemia in *P. falciparum*-infected human red blood cells.

3. An isolated peptide consisting of residues 36-89 of SEQ ID NO. 1 that can bind to a protein selected from the group consisting of PfMSPI-19 and PfMSP1-42.

4. The isolated peptide of claim 1, said peptide is from the organism *Pseudomonas aeruginosa*.

5. The isolated peptide of claim 1, which is fused to SEQ ID NO.21, H.8 region of Laz.

6. A pharmaceutical composition comprising the isolated peptide of claim 1 in a pharmaceutically acceptable carrier composition.

7. The composition of claim 6, additionally comprises an anti-malarial drug.

8. The composition of claim 6, wherein the isolated peptide is from *Pseudomonas aeruginosa*.

* * * * *

UNITED STATES PATENT AND TRADEMARK OFFICE
CERTIFICATE OF CORRECTION

PATENT NO. : 7,338,766 B2  Page 1 of 1
APPLICATION NO. : 11/436590
DATED : March 4, 2008
INVENTOR(S) : Ananda Chakrabarty et al.

It is certified that error appears in the above-identified patent and that said Letters Patent is hereby corrected as shown below:

Claim 3, line 3, "PfMSPI-19" should read --PfMSP1-19--.

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,338,766 B2 | Page 1 of 1 |
| APPLICATION NO. | : 11/436590 | |
| DATED | : March 4, 2008 | |
| INVENTOR(S) | : Ananda Chakrabarty et al. | |

It is certified that error appears in the above-identified patent and that said Letters Patent is hereby corrected as shown below:

Column 1, lines 28-34:
"STATEMENT OF GOVERNMENTAL INTEREST
The subject matter of this application has been supported by research grants from the National Institutes of Health (NIH), Bethesda, Maryland, U.S.A., (Grant Numbers AI 16790-21, ES 04050-16, AI 45541, CA09432 and N01-CM97567). The government may have certain rights in this invention." should be deleted.

Signed and Sealed this

Seventeenth Day of August, 2010

David J. Kappos
*Director of the United States Patent and Trademark Office*

SEQUENCE LISTING

```
<160> NUMBER OF SEQ ID NOS: 36

<210> SEQ ID NO 1
<211> LENGTH: 128
<212> TYPE: PRT
<213> ORGANISM: Pseudomonas aeruginosa

<400> SEQUENCE: 1

Ala Glu Cys Ser Val Asp Ile Gln Gly Asn Asp Gln Met Gln Phe Asn
1               5                   10                  15

Thr Asn Ala Ile Thr Val Asp Lys Ser Cys Lys Gln Phe Thr Val Asn
            20                  25                  30

Leu Ser His Pro Gly Asn Leu Pro Lys Asn Val Met Gly His Asn Trp
        35                  40                  45

Val Leu Ser Thr Ala Ala Asp Met Gln Gly Val Val Thr Asp Gly Met
    50                  55                  60

Ala Ser Gly Leu Asp Lys Asp Tyr Leu Lys Pro Asp Asp Ser Arg Val
65                  70                  75                  80

Ile Ala His Thr Lys Leu Ile Gly Ser Gly Glu Lys Asp Ser Val Thr
                85                  90                  95

Phe Asp Val Ser Lys Leu Lys Glu Gly Glu Gln Tyr Met Phe Phe Cys
            100                 105                 110

Thr Phe Pro Gly His Ser Ala Leu Met Lys Gly Thr Leu Thr Leu Lys
        115                 120                 125

<210> SEQ ID NO 2
<211> LENGTH: 82
<212> TYPE: PRT
<213> ORGANISM: Pseudomonas aeruginosa

<400> SEQUENCE: 2

Glu Asp Pro Glu Val Leu Phe Lys Asn Lys Gly Cys Val Ala Cys His
1               5                   10                  15

Ala Ile Asp Thr Lys Met Val Gly Pro Ala Tyr Lys Asp Val Ala Ala
            20                  25                  30

Lys Phe Ala Gly Gln Ala Gly Ala Glu Ala Glu Leu Ala Gln Arg Ile
        35                  40                  45

Lys Asn Gly Ser Gln Gly Val Trp Gly Pro Ile Pro Met Pro Pro Asn
    50                  55                  60

Ala Val Ser Asp Asp Glu Ala Gln Thr Leu Ala Lys Trp Val Leu Ser
65                  70                  75                  80

Gln Lys

<210> SEQ ID NO 3
<211> LENGTH: 166
```

```
<212> TYPE: PRT
<213> ORGANISM: Neisseria meningitidis

<400> SEQUENCE: 3

Cys Ser Gln Glu Pro Ala Ala Pro Ala Ala Glu Ala Thr Pro Ala Ala
1               5                   10                  15

Glu Ala Pro Ala Ser Glu Ala Pro Ala Glu Ala Ala Pro Ala Asp
            20                  25                  30

Ala Ala Glu Ala Pro Ala Ala Gly Asn Cys Ala Ala Thr Val Glu Ser
            35                  40                  45

Asn Asp Asn Met Gln Phe Asn Thr Lys Asp Ile Gln Val Ser Lys Ala
50                  55                  60

Cys Lys Glu Phe Thr Ile Thr Leu Lys His Thr Gly Thr Gln Pro Lys
65                  70                  75                  80

Ala Ser Met Gly His Asn Leu Val Ile Ala Lys Ala Glu Asp Met Asp
                85                  90                  95

Gly Val Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
            115                 120                 125

Glu Glu Ala Ser Leu Thr Leu Asp Pro Ala Lys Leu Ala Asp Gly Glu
130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 4
<211> LENGTH: 105
<212> TYPE: PRT
<213> ORGANISM: Phormidium laminosum

<400> SEQUENCE: 4

Glu Thr Phe Thr Val Lys Met Gly Ala Asp Ser Gly Leu Leu Gln Phe
1               5                   10                  15

Glu Pro Ala Asn Val Thr Val His Pro Gly Asp Thr Val Lys Trp Val
            20                  25                  30

Asn Asn Lys Leu Pro Pro His Asn Ile Leu Phe Asp Asp Lys Gln Val
            35                  40                  45

Pro Gly Ala Ser Lys Glu Leu Ala Asp Lys Leu Ser His Ser Gln Leu
50                  55                  60

Met Phe Ser Pro Gly Glu Ser Tyr Glu Ile Thr Phe Ser Ser Asp Phe
65                  70                  75                  80

Pro Ala Gly Thr Tyr Thr Tyr Tyr Cys Ala Pro His Arg Gly Ala Gly
                85                  90                  95

Met Val Gly Lys Ile Thr Val Glu Gly
            100                 105

<210> SEQ ID NO 5
<211> LENGTH: 155
<212> TYPE: PRT
<213> ORGANISM: Thiobacillus ferrooxidans

<400> SEQUENCE: 5

Gly Thr Leu Asp Thr Thr Trp Lys Glu Ala Thr Leu Pro Gln Val Lys
1               5                   10                  15

Ala Met Leu Glu Lys Asp Thr Gly Lys Val Ser Gly Asp Thr Val Thr
```

-continued

```
                    20                  25                  30
Tyr Ser Gly Lys Thr Val His Val Ala Ala Val Leu Pro Gly
            35                  40                  45

Phe Pro Phe Pro Ser Phe Glu Val His Asp Lys Lys Asn Pro Thr Leu
         50                  55                  60

Glu Ile Pro Ala Gly Ala Thr Val Asp Val Thr Phe Ile Asn Thr Asn
 65                  70                  75                  80

Lys Gly Phe Gly His Ser Phe Asp Ile Thr Lys Lys Gly Pro Pro Tyr
                 85                  90                  95

Ala Val Met Pro Val Ile Asp Pro Ile Val Ala Gly Thr Gly Phe Ser
            100                 105                 110

Pro Val Pro Lys Asp Gly Lys Phe Gly Tyr Thr Asp Phe Thr Trp His
        115                 120                 125

Pro Thr Ala Gly Thr Tyr Tyr Tyr Val Cys Gln Ile Pro Gly His Ala
    130                 135                 140

Ala Thr Gly Met Phe Gly Lys Ile Val Val Lys
145                 150                 155

<210> SEQ ID NO 6
<211> LENGTH: 124
<212> TYPE: PRT
<213> ORGANISM: Achromabacter cycloclastes

<400> SEQUENCE: 6

Ala Asp Phe Glu Val His Met Leu Asn Lys Gly Lys Asp Gly Ala Met
 1               5                  10                  15

Val Phe Glu Pro Ala Ser Leu Lys Val Ala Pro Gly Asp Thr Val Thr
                20                  25                  30

Phe Ile Pro Thr Asp Lys Gly His Asn Val Glu Thr Ile Lys Gly Met
            35                  40                  45

Ile Pro Asp Gly Ala Glu Ala Phe Lys Ser Lys Ile Asn Glu Asn Tyr
        50                  55                  60

Lys Val Thr Phe Thr Ala Pro Gly Val Tyr Gly Val Lys Cys Thr Pro
 65                  70                  75                  80

His Tyr Gly Met Gly Met Val Gly Val Gln Val Gly Asp Ala Pro
                85                  90                  95

Ala Asn Leu Glu Ala Val Lys Gly Ala Lys Asn Pro Lys Lys Ala Gln
            100                 105                 110

Glu Arg Leu Asp Ala Ala Leu Ala Ala Leu Gly Asn
        115                 120

<210> SEQ ID NO 7
<211> LENGTH: 128
<212> TYPE: PRT
<213> ORGANISM: Alcaligenes faecalis

<400> SEQUENCE: 7

Ala Cys Asp Val Ser Ile Glu Gly Asn Asp Ser Met Gln Phe Asn Thr
 1               5                  10                  15

Lys Ser Ile Val Val Asp Lys Thr Cys Lys Glu Phe Thr Ile Asn Leu
                20                  25                  30

Lys His Thr Gly Lys Leu Pro Lys Ala Ala Met Gly His Asn Val Val
            35                  40                  45

Val Ser Lys Lys Ser Asp Glu Ser Ala Val Ala Thr Asp Gly Met Lys
        50                  55                  60

Ala Gly Leu Asn Asn Asp Tyr Val Lys Ala Gly Asp Glu Arg Val Ile
```

```
                65                  70                  75                  80
Ala His Thr Ser Val Ile Gly Gly Glu Thr Asp Ser Val Thr Phe
                    85                  90                  95

Asp Val Ser Lys Leu Lys Glu Gly Glu Asp Tyr Ala Phe Phe Cys Ser
                100                 105                 110

Phe Pro Gly His Trp Ser Ile Met Lys Gly Thr Ile Glu Leu Gly Ser
                115                 120                 125

<210> SEQ ID NO 8
<211> LENGTH: 129
<212> TYPE: PRT
<213> ORGANISM: Achromobacter xylosoxidans ssp. denitrificans I

<400> SEQUENCE: 8

Ala Gln Cys Glu Ala Thr Ile Glu Ser Asn Asp Ala Met Gln Tyr Asn
1               5                   10                  15

Leu Lys Glu Met Val Val Asp Lys Ser Cys Lys Gln Phe Thr Val His
                20                  25                  30

Leu Lys His Val Gly Lys Met Ala Lys Val Ala Met Gly His Asn Trp
            35                  40                  45

Val Leu Thr Lys Glu Ala Asp Lys Gln Gly Val Ala Thr Asp Gly Met
50                  55                  60

Asn Ala Gly Leu Ala Gln Asp Tyr Val Lys Ala Gly Asp Thr Arg Val
65                  70                  75                  80

Ile Ala His Thr Lys Val Ile Gly Gly Gly Glu Ser Asp Ser Val Thr
                85                  90                  95

Phe Asp Val Ser Lys Leu Thr Pro Gly Glu Ala Tyr Ala Tyr Phe Cys
                100                 105                 110

Ser Phe Pro Gly His Trp Ala Met Met Lys Gly Thr Leu Lys Leu Ser
                115                 120                 125

Asn

<210> SEQ ID NO 9
<211> LENGTH: 129
<212> TYPE: PRT
<213> ORGANISM: Bordetella bronchiseptica

<400> SEQUENCE: 9

Ala Glu Cys Ser Val Asp Ile Ala Gly Thr Asp Gln Met Gln Phe Asp
1               5                   10                  15

Lys Lys Ala Ile Glu Val Ser Lys Ser Cys Lys Gln Phe Thr Val Asn
                20                  25                  30

Leu Lys His Thr Gly Lys Leu Pro Arg Asn Val Met Gly His Asn Trp
            35                  40                  45

Val Leu Thr Lys Thr Ala Asp Met Gln Ala Val Glu Lys Asp Gly Ile
50                  55                  60

Ala Ala Gly Leu Asp Asn Gln Tyr Leu Lys Ala Gly Asp Thr Arg Val
65                  70                  75                  80

Leu Ala His Thr Lys Val Leu Gly Gly Gly Glu Ser Asp Ser Val Thr
                85                  90                  95

Phe Asp Val Ala Lys Leu Ala Ala Gly Asp Asp Tyr Thr Phe Phe Cys
                100                 105                 110

Ser Phe Pro Gly His Gly Ala Leu Met Lys Gly Thr Leu Lys Leu Val
                115                 120                 125

Asp
```

<210> SEQ ID NO 10
<211> LENGTH: 129
<212> TYPE: PRT
<213> ORGANISM: Methylomonas sp. J.

<400> SEQUENCE: 10

Ala Ser Cys Glu Thr Thr Val Thr Ser Gly Asp Thr Met Thr Tyr Ser
1               5                   10                  15

Thr Arg Ser Ile Ser Val Pro Ala Ser Cys Ala Glu Phe Thr Val Asn
            20                  25                  30

Phe Glu His Lys Gly His Met Pro Lys Thr Gly Met Gly His Asn Trp
        35                  40                  45

Val Leu Ala Lys Ser Ala Asp Val Gly Asp Val Ala Lys Glu Gly Ala
    50                  55                  60

His Ala Gly Ala Asp Asn Asn Phe Val Thr Pro Gly Asp Lys Arg Val
65                  70                  75                  80

Ile Ala Phe Thr Pro Ile Ile Gly Gly Gly Lys Thr Ser Val Lys
                85                  90                  95

Phe Lys Val Ser Ala Leu Ser Lys Asp Glu Ala Tyr Thr Tyr Phe Cys
            100                 105                 110

Ser Tyr Pro Gly His Phe Ser Met Met Arg Gly Thr Leu Lys Leu Glu
        115                 120                 125

Glu

<210> SEQ ID NO 11
<211> LENGTH: 166
<212> TYPE: PRT
<213> ORGANISM: Neisseria meningitidis

<400> SEQUENCE: 11

Cys Ser Gln Glu Pro Ala Ala Pro Ala Ala Glu Ala Thr Pro Ala Ala
1               5                   10                  15

Glu Ala Pro Ala Ser Glu Ala Pro Ala Ala Glu Ala Ala Pro Ala Asp
            20                  25                  30

Ala Ala Glu Ala Pro Ala Ala Gly Asn Cys Ala Ala Thr Val Glu Ser
        35                  40                  45

Asn Asp Asn Met Gln Phe Asn Thr Lys Asp Ile Gln Val Ser Lys Ala
    50                  55                  60

Cys Lys Glu Phe Thr Ile Thr Leu Lys His Thr Gly Thr Gln Pro Lys
65                  70                  75                  80

Thr Ser Met Gly His Asn Ile Val Ile Gly Lys Thr Glu Asp Met Asp
                85                  90                  95

Gly Ile Phe Lys Asp Gly Val Gly Ala Ala Asp Thr Asp Tyr Val Lys
            100                 105                 110

Pro Asp Asp Ala Arg Val Val Ala His Thr Lys Leu Ile Gly Gly Gly
        115                 120                 125

Glu Glu Ser Ser Leu Thr Leu Asp Pro Ala Lys Leu Ala Asp Gly Glu
    130                 135                 140

Tyr Lys Phe Ala Cys Thr Phe Pro Gly His Gly Ala Leu Met Asn Gly
145                 150                 155                 160

Lys Val Thr Leu Val Asp
                165

<210> SEQ ID NO 12
<211> LENGTH: 128
<212> TYPE: PRT

-continued

<213> ORGANISM: Pseudomomas fluorescens

<400> SEQUENCE: 12

Ala Glu Cys Lys Thr Thr Ile Asp Ser Thr Asp Gln Met Ser Phe Asn
1               5                   10                  15

Thr Lys Ala Ile Glu Ile Asp Lys Ala Cys Lys Thr Phe Thr Val Glu
            20                  25                  30

Leu Thr His Ser Gly Ser Leu Pro Lys Asn Val Met Gly His Asn Leu
        35                  40                  45

Val Ile Ser Lys Gln Ala Asp Met Gln Pro Ile Ala Thr Asp Gly Leu
50                  55                  60

Ser Ala Gly Ile Asp Lys Asn Tyr Leu Lys Glu Gly Asp Thr Arg Val
65                  70                  75                  80

Ile Ala His Thr Lys Val Ile Gly Ala Gly Glu Lys Asp Ser Leu Thr
                85                  90                  95

Ile Asp Val Ser Lys Leu Asn Ala Ala Glu Lys Tyr Gly Phe Phe Cys
            100                 105                 110

Ser Phe Pro Gly His Ile Ser Met Met Lys Gly Thr Val Thr Leu Lys
        115                 120                 125

<210> SEQ ID NO 13
<211> LENGTH: 128
<212> TYPE: PRT
<213> ORGANISM: Pseudomonas chlororaphis

<400> SEQUENCE: 13

Ala Glu Cys Lys Val Asp Val Asp Ser Thr Asp Gln Met Ser Phe Asn
1               5                   10                  15

Thr Lys Glu Ile Thr Ile Asp Lys Ser Cys Lys Thr Phe Thr Val Asn
            20                  25                  30

Leu Thr His Ser Gly Ser Leu Pro Lys Asn Val Met Gly His Asn Trp
        35                  40                  45

Val Leu Ser Lys Ser Ala Asp Met Ala Gly Ile Ala Thr Asp Gly Met
50                  55                  60

Ala Ala Gly Ile Asp Lys Asp Tyr Leu Lys Pro Gly Asp Ser Arg Val
65                  70                  75                  80

Ile Ala His Thr Lys Ile Ile Gly Ser Gly Glu Lys Asp Ser Val Thr
                85                  90                  95

Phe Asp Val Ser Lys Leu Thr Ala Gly Glu Ser Tyr Glu Phe Phe Cys
            100                 105                 110

Ser Phe Pro Gly His Asn Ser Met Met Lys Gly Ala Val Val Leu Lys
        115                 120                 125

<210> SEQ ID NO 14
<211> LENGTH: 129
<212> TYPE: PRT
<213> ORGANISM: Xylella fastidiosa 9a5c

<400> SEQUENCE: 14

Lys Thr Cys Ala Val Thr Ile Ser Ala Asn Asp Gln Met Lys Phe Asp
1               5                   10                  15

Gln Asn Thr Ile Lys Ile Ala Ala Glu Cys Thr His Val Asn Leu Thr
            20                  25                  30

Leu Thr His Thr Gly Lys Lys Ser Ala Arg Val Met Gly His Asn Trp
        35                  40                  45

Val Leu Thr Lys Thr Thr Asp Met Gln Ala Val Ala Leu Ala Gly Leu
50                  55                  60

His Ala Thr Leu Ala Asp Asn Tyr Val Pro Lys Ala Asp Pro Arg Val
65                  70                  75                  80

Ile Ala His Thr Ala Ile Ile Gly Gly Gly Glu Arg Thr Ser Ile Thr
                85                  90                  95

Phe Pro Thr Asn Thr Leu Ser Lys Asn Val Ser Tyr Thr Phe Phe Cys
            100                 105                 110

Ser Phe Pro Gly His Trp Ala Leu Met Lys Gly Thr Leu Asn Phe Gly
        115                 120                 125

Gly

<210> SEQ ID NO 15
<211> LENGTH: 138
<212> TYPE: PRT
<213> ORGANISM: Cucumis sativus

<400> SEQUENCE: 15

Met Gln Ser Thr Val His Ile Val Gly Asp Asn Thr Gly Trp Ser Val
1               5                   10                  15

Pro Ser Ser Pro Asn Phe Tyr Ser Gln Trp Ala Ala Gly Lys Thr Phe
            20                  25                  30

Arg Val Gly Asp Ser Leu Gln Phe Asn Phe Pro Ala Asn Ala His Asn
        35                  40                  45

Val His Glu Met Glu Thr Lys Gln Ser Phe Asp Ala Cys Asn Phe Val
    50                  55                  60

Asn Ser Asp Asn Asp Val Glu Arg Thr Ser Pro Val Ile Glu Arg Leu
65                  70                  75                  80

Asp Glu Leu Gly Met His Tyr Phe Val Cys Thr Val Gly Thr His Cys
                85                  90                  95

Ser Asn Gly Gln Lys Leu Ser Ile Asn Val Val Ala Ala Asn Ala Thr
            100                 105                 110

Val Ser Met Pro Pro Ser Ser Pro Ser Ser Val Met Pro
        115                 120                 125

Pro Pro Val Met Pro Pro Ser Pro Ser
    130                 135

<210> SEQ ID NO 16
<211> LENGTH: 162
<212> TYPE: PRT
<213> ORGANISM: Chloroflexus aurantiacus

<400> SEQUENCE: 16

Met Lys Ile Thr Leu Arg Met Met Val Leu Ala Val Leu Thr Ala Met
1               5                   10                  15

Ala Met Val Leu Ala Ala Cys Gly Gly Gly Ser Gly Gly Ser
            20                  25                  30

Thr Gly Gly Gly Ser Gly Ser Gly Pro Val Thr Ile Glu Ile Gly Ser
        35                  40                  45

Lys Gly Glu Glu Leu Ala Phe Asp Lys Thr Glu Leu Thr Val Ser Ala
    50                  55                  60

Gly Gln Thr Val Thr Ile Arg Phe Lys Asn Asn Ser Ala Val Gln Gln
65                  70                  75                  80

His Asn Trp Ile Leu Val Lys Gly Gly Glu Ala Glu Ala Ala Asn Ile
                85                  90                  95

Ala Asn Ala Gly Leu Ser Ala Gly Pro Ala Ala Asn Tyr Leu Pro Ala
            100                 105                 110

```
Asp Lys Ser Asn Ile Ile Ala Glu Ser Pro Leu Ala Asn Gly Asn Glu
            115                 120                 125

Thr Val Glu Val Thr Phe Thr Ala Pro Ala Ala Gly Thr Tyr Leu Tyr
        130                 135                 140

Ile Cys Thr Val Pro Gly His Tyr Pro Leu Met Gln Gly Lys Leu Val
145                 150                 155                 160

Val Asn

<210> SEQ ID NO 17
<211> LENGTH: 140
<212> TYPE: PRT
<213> ORGANISM: Chloroflexus aurantiacus

<400> SEQUENCE: 17

Ala Ala Asn Ala Pro Gly Gly Ser Asn Val Asn Glu Thr Pro Ala
1               5                   10                  15

Gln Thr Val Glu Val Arg Ala Ala Pro Asp Ala Leu Ala Phe Ala Gln
            20                  25                  30

Thr Ser Leu Ser Leu Pro Ala Asn Thr Val Val Arg Leu Asp Phe Val
        35                  40                  45

Asn Gln Asn Asn Leu Gly Val Gln His Asn Trp Val Leu Val Asn Gly
    50                  55                  60

Gly Asp Asp Val Ala Ala Ala Val Asn Thr Ala Ala Gln Asn Asn Ala
65                  70                  75                  80

Asp Ala Leu Phe Val Pro Pro Asp Thr Pro Asn Ala Leu Ala Trp
                85                  90                  95

Thr Ala Met Leu Asn Ala Gly Glu Ser Gly Ser Val Thr Phe Arg Thr
            100                 105                 110

Pro Ala Pro Gly Thr Tyr Leu Tyr Ile Cys Thr Phe Pro Gly His Tyr
        115                 120                 125

Leu Ala Gly Met Lys Gly Thr Leu Thr Val Thr Pro
    130                 135                 140

<210> SEQ ID NO 18
<211> LENGTH: 96
<212> TYPE: PRT
<213> ORGANISM: Cucumis sativus

<400> SEQUENCE: 18

Ala Val Tyr Val Val Gly Gly Ser Gly Gly Trp Thr Phe Asn Thr Glu
1               5                   10                  15

Ser Trp Pro Lys Gly Lys Arg Phe Arg Ala Gly Asp Ile Leu Leu Phe
            20                  25                  30

Asn Tyr Asn Pro Ser Met His Asn Val Val Val Asn Gln Gly Gly
        35                  40                  45

Phe Ser Thr Cys Asn Thr Pro Ala Gly Ala Lys Val Tyr Thr Ser Gly
    50                  55                  60

Arg Asp Gln Ile Lys Leu Pro Lys Gly Gln Ser Tyr Phe Ile Cys Asn
65                  70                  75                  80

Phe Pro Gly His Cys Gln Ser Gly Met Lys Ile Ala Val Asn Ala Leu
                85                  90                  95

<210> SEQ ID NO 19
<211> LENGTH: 104
<212> TYPE: PRT
<213> ORGANISM: Homo sapiens

<400> SEQUENCE: 19
```

Gly Asp Val Glu Lys Gly Lys Ile Phe Ile Met Lys Cys Ser Gln
1               5                   10                  15

Cys His Thr Val Glu Lys Gly Lys His Lys Thr Gly Pro Asn Leu
                20                  25                  30

His Gly Leu Phe Gly Arg Lys Thr Gly Gln Ala Pro Gly Tyr Ser Tyr
            35                  40                  45

Thr Ala Ala Asn Lys Asn Lys Gly Ile Ile Trp Gly Glu Asp Thr Leu
    50                  55                  60

Met Glu Tyr Leu Glu Asn Pro Lys Lys Tyr Ile Pro Gly Thr Lys Met
65                  70                  75                  80

Ile Phe Val Gly Ile Lys Lys Lys Glu Glu Arg Ala Asp Leu Ile Ala
                85                  90                  95

Tyr Leu Lys Lys Ala Thr Asn Glu
            100

<210> SEQ ID NO 20
<211> LENGTH: 338
<212> TYPE: PRT
<213> ORGANISM: Phormidium laminosum

<400> SEQUENCE: 20

Met Asn Phe Lys Val Cys Ser Phe Pro Ser Arg Arg Gln Ser Ile Ala
1               5                   10                  15

Ala Phe Val Arg Val Leu Met Val Ile Leu Leu Thr Leu Gly Ala Leu
                20                  25                  30

Val Ser Ser Asp Val Leu Leu Pro Gln Pro Ala Ala Ala Tyr Pro Phe
            35                  40                  45

Trp Ala Gln Gln Asn Tyr Ala Asn Pro Arg Glu Ala Thr Gly Arg Ile
    50                  55                  60

Val Cys Ala Asn Cys His Leu Ala Ala Lys Pro Ala Glu Ile Glu Val
65                  70                  75                  80

Pro Gln Ala Val Leu Pro Asp Ser Val Phe Lys Ala Val Lys Ile
                85                  90                  95

Pro Tyr Asp His Ser Val Gln Gln Val Gln Ala Asp Gly Ser Lys Gly
            100                 105                 110

Pro Leu Asn Val Gly Ala Val Leu Met Leu Pro Glu Gly Phe Thr Ile
    115                 120                 125

Ala Pro Glu Asp Arg Ile Pro Glu Glu Met Lys Glu Glu Val Gly Pro
130                 135                 140

Ser Tyr Leu Phe Gln Pro Tyr Ala Asp Asp Lys Gln Asn Ile Val Leu
145                 150                 155                 160

Val Gly Pro Leu Pro Gly Asp Gln Tyr Glu Glu Ile Val Phe Pro Val
                165                 170                 175

Leu Ser Pro Asn Pro Ala Thr Asn Lys Ser Val Ala Phe Gly Lys Tyr
            180                 185                 190

Ser Ile His Leu Gly Ala Asn Arg Gly Arg Gly Gln Ile Tyr Pro Thr
    195                 200                 205

Gly Glu Lys Ser Asn Asn Ala Val Tyr Asn Ala Ser Ala Ala Gly Val
210                 215                 220

Ile Thr Ala Ile Ala Lys Ala Asp Asp Gly Ser Ala Glu Val Lys Ile
225                 230                 235                 240

Arg Thr Glu Asp Gly Thr Thr Ile Val Asp Lys Ile Pro Ala Gly Pro
                245                 250                 255

Glu Leu Ile Val Ser Glu Gly Glu Glu Val Ala Ala Gly Ala Ala Leu

-continued

```
                    260                 265                 270
Thr Asn Asn Pro Asn Val Gly Gly Phe Gly Gln Lys Asp Thr Glu Ile
            275                 280                 285
Val Leu Gln Ser Pro Asn Arg Val Lys Gly Arg Ile Ala Phe Leu Ala
        290                 295                 300
Ala Ile Thr Leu Thr Gln Ile Leu Leu Val Leu Lys Lys Gln Val
305                 310                 315                 320
Glu Arg Val Gln Ala Gly Arg Asp Asp Leu Leu Lys Ala Ala Phe Ile
                325                 330                 335
Ala Gly

<210> SEQ ID NO 21
<211> LENGTH: 39
<212> TYPE: PRT
<213> ORGANISM: Neisseria gonnorrhoeae

<400> SEQUENCE: 21

Cys Ser Gln Glu Pro Ala Ala Pro Ala Ala Glu Ala Thr Pro Ala Gly
1               5                   10                  15
Glu Ala Pro Ala Ser Glu Ala Pro Ala Ala Glu Ala Ala Pro Ala Asp
            20                  25                  30
Ala Ala Glu Ala Pro Ala Ala
        35

<210> SEQ ID NO 22
<211> LENGTH: 166
<212> TYPE: PRT
<213> ORGANISM: Neisseria gonorrhoeae F62

<400> SEQUENCE: 22

Cys Ser Gln Glu Pro Ala Ala Pro Ala Ala Glu Ala Thr Pro Ala Gly
1               5                   10                  15
Glu Ala Pro Ala Ser Glu Ala Pro Ala Ala Glu Ala Ala Pro Ala Asp
            20                  25                  30
Ala Ala Glu Ala Pro Ala Ala Gly Asn Cys Ala Ala Thr Val Glu Ser
        35                  40                  45
Asn Asp Asn Met Gln Phe Asn Thr Lys Asp Ile Gln Val Ser Lys Ala
    50                  55                  60
Cys Lys Glu Phe Thr Ile Thr Leu Lys His Thr Gly Thr Gln Pro Lys
65                  70                  75                  80
Ala Ser Met Gly His Asn Leu Val Ile Ala Lys Ala Glu Asp Met Asp
                85                  90                  95
Gly Val Phe Lys Asp Gly Val Gly Ala Ala Asp Thr Asp Tyr Val Lys
            100                 105                 110
Pro Asp Asp Ala Arg Val Val Ala His Thr Lys Leu Ile Gly Gly Gly
        115                 120                 125
Glu Glu Ser Ser Leu Thr Leu Asp Pro Ala Lys Leu Ala Asp Gly Asp
    130                 135                 140
Tyr Lys Phe Ala Cys Thr Phe Pro Gly His Gly Ala Leu Met Asn Gly
145                 150                 155                 160
Lys Val Thr Leu Val Asp
                165

<210> SEQ ID NO 23
<211> LENGTH: 33
<212> TYPE: DNA
<213> ORGANISM: artificial sequence
```

```
<220> FEATURE:
<223> OTHER INFORMATION: forward primer for Laz

<400> SEQUENCE: 23
ccggaattcc ggcagggatg ttgtaaatat ccg                          33

<210> SEQ ID NO 24
<211> LENGTH: 38
<212> TYPE: DNA
<213> ORGANISM: artificial sequence
<220> FEATURE:
<223> OTHER INFORMATION: PCR primer

<400> SEQUENCE: 24
ggggtaccgc cgtggcaggc atacagcatt tcaatcgg                     38

<210> SEQ ID NO 25
<211> LENGTH: 27
<212> TYPE: DNA
<213> ORGANISM: artificial sequence
<220> FEATURE:
<223> OTHER INFORMATION: PCR primer

<400> SEQUENCE: 25
ggcagcaggg gcttcggcag catctgc                                 27

<210> SEQ ID NO 26
<211> LENGTH: 26
<212> TYPE: DNA
<213> ORGANISM: artificial sequence
<220> FEATURE:
<223> OTHER INFORMATION: PCR primer

<400> SEQUENCE: 26
ctgcaggtcg actctagagg atcccg                                  26

<210> SEQ ID NO 27
<211> LENGTH: 25
<212> TYPE: DNA
<213> ORGANISM: artificial sequence
<220> FEATURE:
<223> OTHER INFORMATION: PCR primer

<400> SEQUENCE: 27
gccgagtgct cggtggacat ccagg                                   25

<210> SEQ ID NO 28
<211> LENGTH: 27
<212> TYPE: DNA
<213> ORGANISM: artificial sequence
<220> FEATURE:
<223> OTHER INFORMATION: PCR primer

<400> SEQUENCE: 28
tactcgagtc acttcagggt cagggtg                                 27

<210> SEQ ID NO 29
<211> LENGTH: 37
<212> TYPE: DNA
<213> ORGANISM: Artificial sequence
<220> FEATURE:
<223> OTHER INFORMATION: forward primer for pGST-azu 36-128

<400> SEQUENCE: 29
cgggatcccc ggcaacctgc cgaagaacgt catgggc                      37
```

<210> SEQ ID NO 30
<211> LENGTH: 28
<212> TYPE: DNA
<213> ORGANISM: Artificial sequence
<220> FEATURE:
<223> OTHER INFORMATION: reverse primer for pGST-azu 36-128

<400> SEQUENCE: 30
cggaattcgc atcacttcag ggtcaggg                                28

<210> SEQ ID NO 31
<211> LENGTH: 38
<212> TYPE: DNA
<213> ORGANISM: Artificial sequence
<220> FEATURE:
<223> OTHER INFORMATION: forward oligonucleotide for pGST-azu 36-89

<400> SEQUENCE: 31
ccaagctgat cggctcgtga gagaaggact cggtgacc                     38

<210> SEQ ID NO 32
<211> LENGTH: 38
<212> TYPE: DNA
<213> ORGANISM: Artificial sequence
<220> FEATURE:
<223> OTHER INFORMATION: reverse oligonucleotide for pGST-azu 36-89

<400> SEQUENCE: 32
ggtcaccgag tccttctctc acgagccgat cagcttgg                     38

<210> SEQ ID NO 33
<211> LENGTH: 29
<212> TYPE: DNA
<213> ORGANISM: artificial sequence
<220> FEATURE:
<223> OTHER INFORMATION: PCR primer

<400> SEQUENCE: 33
cggggatccc cggctcgggc gagaaggac                               29

<210> SEQ ID NO 34
<211> LENGTH: 29
<212> TYPE: DNA
<213> ORGANISM: artificial sequence
<220> FEATURE:
<223> OTHER INFORMATION: PCR primer

<400> SEQUENCE: 34
cgggaattct ccacttcagg gtcagggtg                               29

<210> SEQ ID NO 35
<211> LENGTH: 29
<212> TYPE: DNA
<213> ORGANISM: artificial sequence
<220> FEATURE:
<223> OTHER INFORMATION: PCR primer

<400> SEQUENCE: 35
gttcttctgc acctagccgg gccactccg                               29

<210> SEQ ID NO 36
<211> LENGTH: 29
<212> TYPE: DNA
<213> ORGANISM: artificial sequence
<220> FEATURE:
<223> OTHER INFORMATION: PCR primer

```
<400> SEQUENCE: 36
cggagtggcc cggctaggtg cagaagaac                                29
```